US012558543B2

(12) United States Patent
Eder

(10) Patent No.: US 12,558,543 B2
(45) Date of Patent: Feb. 24, 2026

(54) SOUND PROCESSING TECHNIQUES

(71) Applicant: Cochlear Limited, Macquarie University (AU)

(72) Inventor: Helmut Christian Eder, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 929 days.

(21) Appl. No.: 17/261,654

(22) PCT Filed: Sep. 4, 2019

(86) PCT No.: PCT/IB2019/057440
§ 371 (c)(1),
(2) Date: Jan. 20, 2021

(87) PCT Pub. No.: WO2020/049472
PCT Pub. Date: Mar. 12, 2020

(65) Prior Publication Data
US 2021/0260377 A1 Aug. 26, 2021

Related U.S. Application Data

(60) Provisional application No. 62/726,728, filed on Sep. 4, 2018.

(51) Int. Cl.
*A61N 1/36* (2006.01)
*H04R 25/00* (2006.01)

(52) U.S. Cl.
CPC ....... *A61N 1/36038* (2017.08); *H04R 25/507* (2013.01); *H04R 25/554* (2013.01);
(Continued)

(58) Field of Classification Search
None
See application file for complete search history.

(56) References Cited

U.S. PATENT DOCUMENTS 8,996,120 B1 * 3/2015 Calle .................. A61N 1/36039
607/57
9,055,377 B2 * 6/2015 Kinsbergen ......... H04M 1/2475
(Continued)

FOREIGN PATENT DOCUMENTS

KR 20120108830 A 10/2012

OTHER PUBLICATIONS

Tobias Goehring et al., "Speech enhancement based on neural networks improves speech intelligibility in noise for cochlear implant users," Hearing Research, Feb. 2017, pp. 183-194, vol. 344.
(Continued)

*Primary Examiner* — Carl H Layno
*Assistant Examiner* — Manolis Pahakis
(74) *Attorney, Agent, or Firm* — Pilloff Passino & Cosenza LLP; Martin J. Cosenza

(57) ABSTRACT

A method, wherein the method includes obtaining data, wherein, the data contains audio content, visual content, or audio content and visual content processing data based on the audio and/or visual content using results from machine learning to develop output, and stimulating tissue of a recipient to evoke a sensory percept based on the output.

19 Claims, 13 Drawing Sheets

(52) U.S. Cl.
CPC ........ *H04R 25/606* (2013.01); *A61N 1/36046*
(2013.01); *H04R 2225/55* (2013.01)

(56) References Cited

U.S. PATENT DOCUMENTS

| | | | |
|---|---|---|---|
| 10,249,318 B2 * | 4/2019 | Kaniewska | G10L 21/0388 |
| 2005/0129262 A1 * | 6/2005 | Dillon | A61N 1/36038 |
| | | | 381/328 |
| 2012/0243695 A1 | 9/2012 | Sohn et al. | |
| 2013/0006328 A1 | 1/2013 | Bouchataoui et al. | |
| 2013/0022223 A1 * | 1/2013 | Kehtarnavaz | A61N 1/0541 |
| | | | 381/317 |
| 2013/0044889 A1 * | 2/2013 | Jensen | H04R 25/356 |
| | | | 381/60 |
| 2014/0058478 A1 * | 2/2014 | Fruhauf | A61N 1/36038 |
| | | | 607/57 |
| 2014/0105434 A1 | 4/2014 | Goorevich et al. | |
| 2014/0336448 A1 * | 11/2014 | Banna | A61N 1/36038 |
| | | | 607/57 |
| 2014/0355798 A1 * | 12/2014 | Sabin | H04R 25/50 |
| | | | 381/314 |
| 2015/0066499 A1 * | 3/2015 | Wang | G06N 3/084 |
| | | | 704/233 |
| 2015/0271608 A1 * | 9/2015 | Sabin | H04R 25/30 |
| | | | 381/314 |
| 2015/0367132 A1 * | 12/2015 | Milczynski | A61N 1/0541 |
| | | | 607/3 |
| 2016/0099008 A1 * | 4/2016 | Barker | H04R 25/505 |
| | | | 704/233 |
| 2016/0157030 A1 * | 6/2016 | Odame | H04R 25/43 |
| | | | 381/313 |
| 2017/0061978 A1 * | 3/2017 | Wang | G10L 21/0232 |
| 2017/0165487 A1 | 6/2017 | van den Honert | |
| 2017/0230765 A1 * | 8/2017 | Jensen | H04R 25/552 |
| 2018/0160984 A1 * | 6/2018 | Mauger | A61B 5/7275 |
| 2018/0197529 A1 * | 7/2018 | Bekolay | G10L 25/24 |
| 2019/0110135 A1 * | 4/2019 | Jensen | H04R 25/505 |
| 2019/0253813 A1 * | 8/2019 | Pedersen | H04R 25/652 |
| 2019/0394568 A1 * | 12/2019 | Sen | G06N 3/045 |
| 2020/0053486 A1 * | 2/2020 | Jensen | H04R 25/505 |
| 2021/0127215 A1 * | 4/2021 | Goorevich | H04R 25/50 |
| 2021/0174824 A1 * | 6/2021 | Martin | G10L 25/30 |

OTHER PUBLICATIONS

Justin A. Zakis et al., "The Design and Evaluation of a Hearing Aid with Trainable Amplification Parameters," Ear and Hearing, Dec. 2007, pp. 812-830, vol. 28, No. 6.
International Search Report & Written Opinion for PCT/IB2019/057440, mailed Dec. 18, 2019.

* cited by examiner

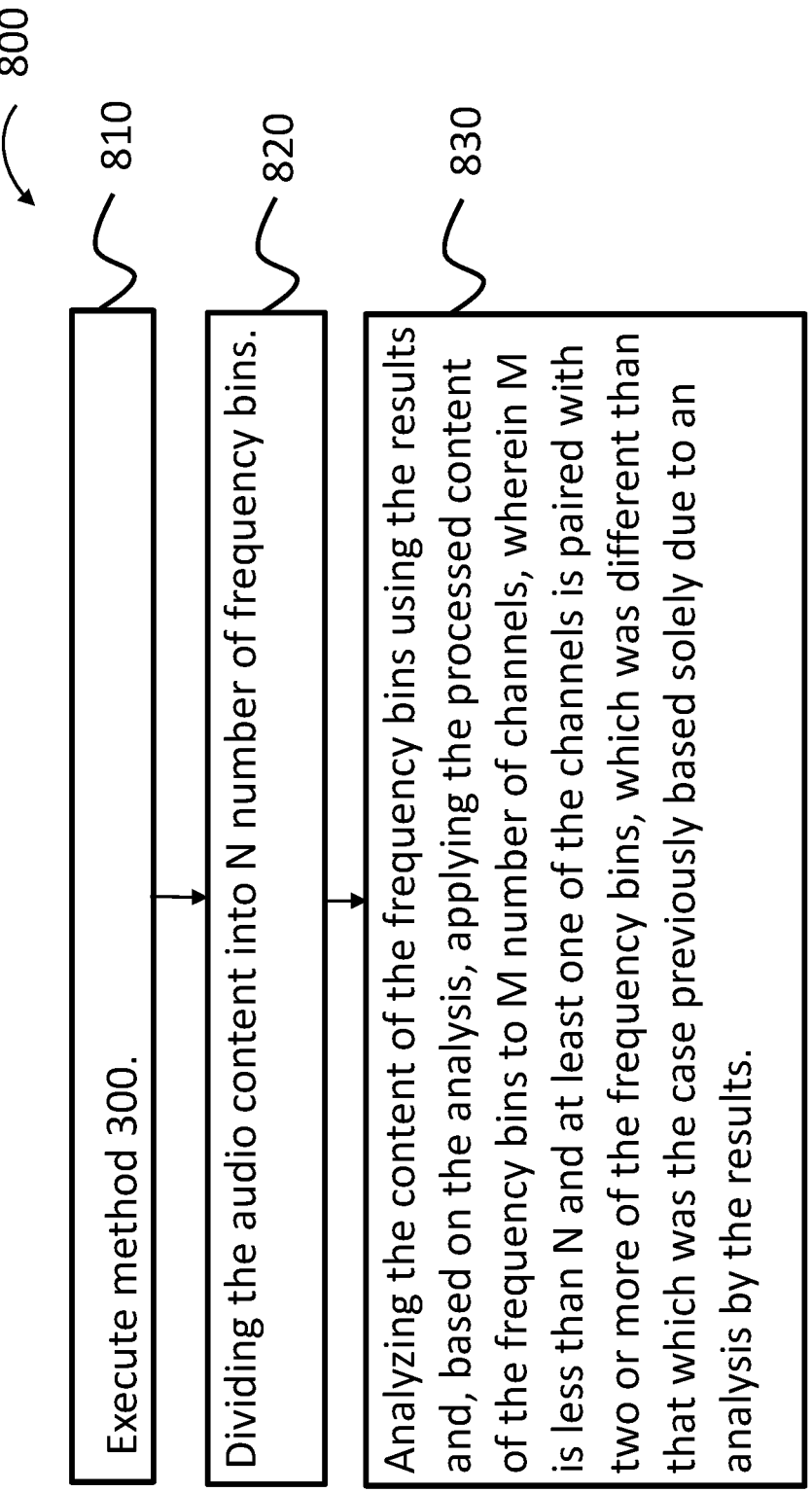

800

810

Execute method 300.

820

Dividing the audio content into N number of frequency bins.

830

Analyzing the content of the frequency bins using the results and, based on the analysis, applying the processed content of the frequency bins to M number of channels, wherein M is less than N and at least one of the channels is paired with two or more of the frequency bins, which was different than that which was the case previously based solely due to an analysis by the results.

FIG. 8

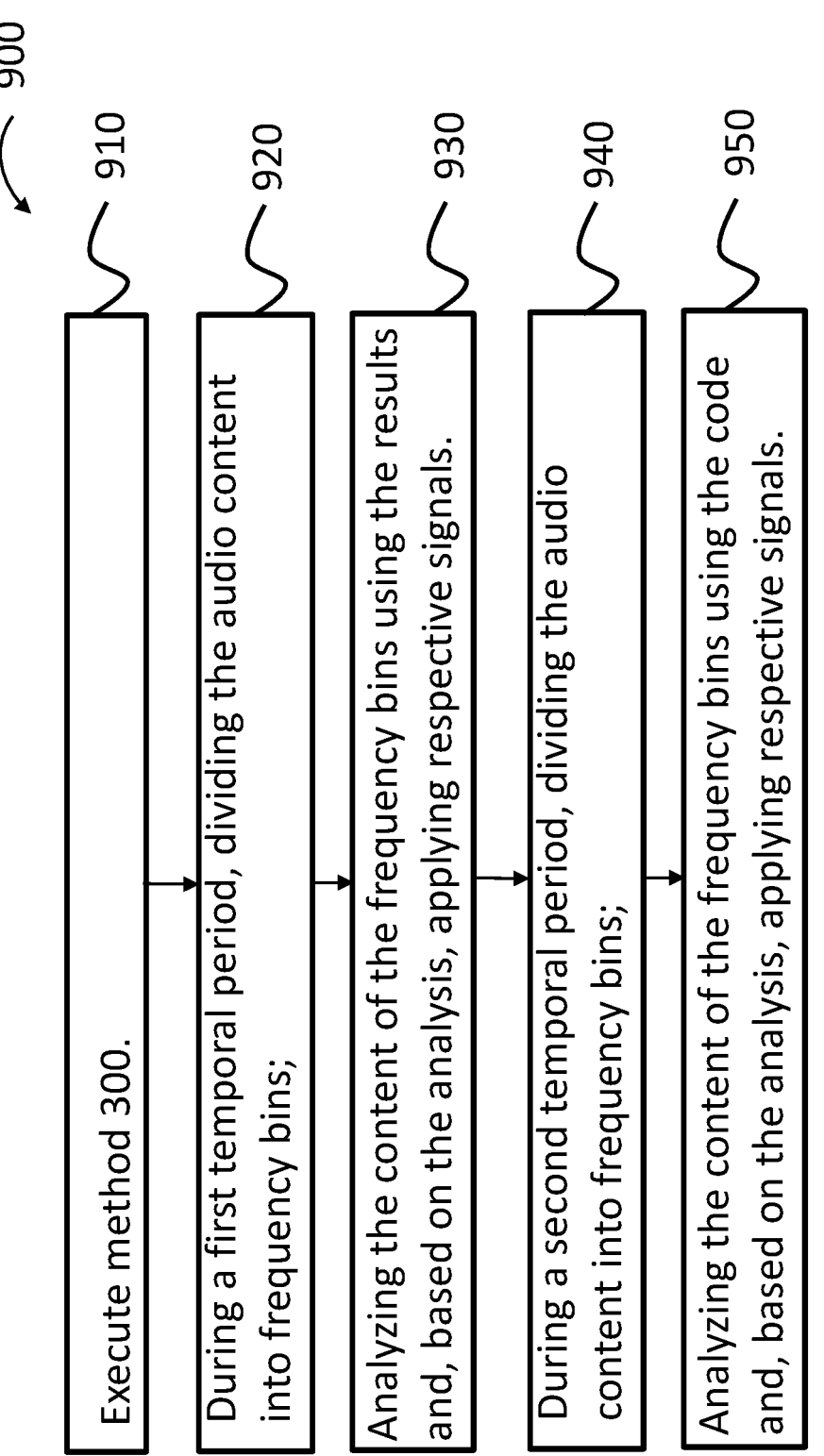

900

910
Execute method 300.

920
During a first temporal period, dividing the audio content into frequency bins;

930
Analyzing the content of the frequency bins using the results and, based on the analysis, applying respective signals.

940
During a second temporal period, dividing the audio content into frequency bins;

950
Analyzing the content of the frequency bins using the code and, based on the analysis, applying respective signals.

FIG. 9

SOUND PROCESSING TECHNIQUES

CROSS-REFERENCE TO RELATED APPLICATIONS

This application claims priority to U.S. Provisional Application No. 62/726,728, entitled NEW SOUND PROCESSING TECHNIQUES, filed on Sep. 4, 2018, naming Helmut Christian EDER of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant. Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound. In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound. Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant.

SUMMARY

In an exemplary embodiment, there is a method, comprising obtaining data containing audio and/or visual content, processing data based on the audio and/or visual content using results from machine learning to develop output and stimulating tissue of a recipient to evoke a sensory percept based on the output.

In an exemplary embodiment, there is a hearing prosthesis including an input subsystem configured to receive input based on sound and an output subsystem configured to stimulate tissue based in input into the input subsystem to evoke a hearing percept and a neural network interposed between the input subsystem and the output subsystem.

In an exemplary embodiment, there is a device, comprising a hearing prosthesis including an input subsystem configured to receive input based on sound and a sound processor configured to process data based on input into the input subsystem, wherein the hearing prosthesis includes a product of and/or resulting from machine learning that is used by the hearing prosthesis to evoke a hearing percept based in input into the input subsystem.

BRIEF DESCRIPTION OF THE DRAWINGS

Embodiments are described below with reference to the attached drawings, in which:

FIG. 8 presents another exemplary flowchart for an exemplary method;

FIG. 9 presents another exemplary flowchart for an exemplary method;

DETAILED DESCRIPTION

Embodiments will be described in terms of a cochlear implant, but it is to be noted that the teachings detailed herein can be applicable to other types of hearing prostheses, and other types of sensory prostheses as well, such as, for example, retinal implants, etc. In an exemplary embodiment of a cochlear implant and an exemplary embodiment of system that utilizes a cochlear implant with other components will first be described, where the implant and the system can be utilized to implement at least some of the teachings detailed herein.

Figure 1:
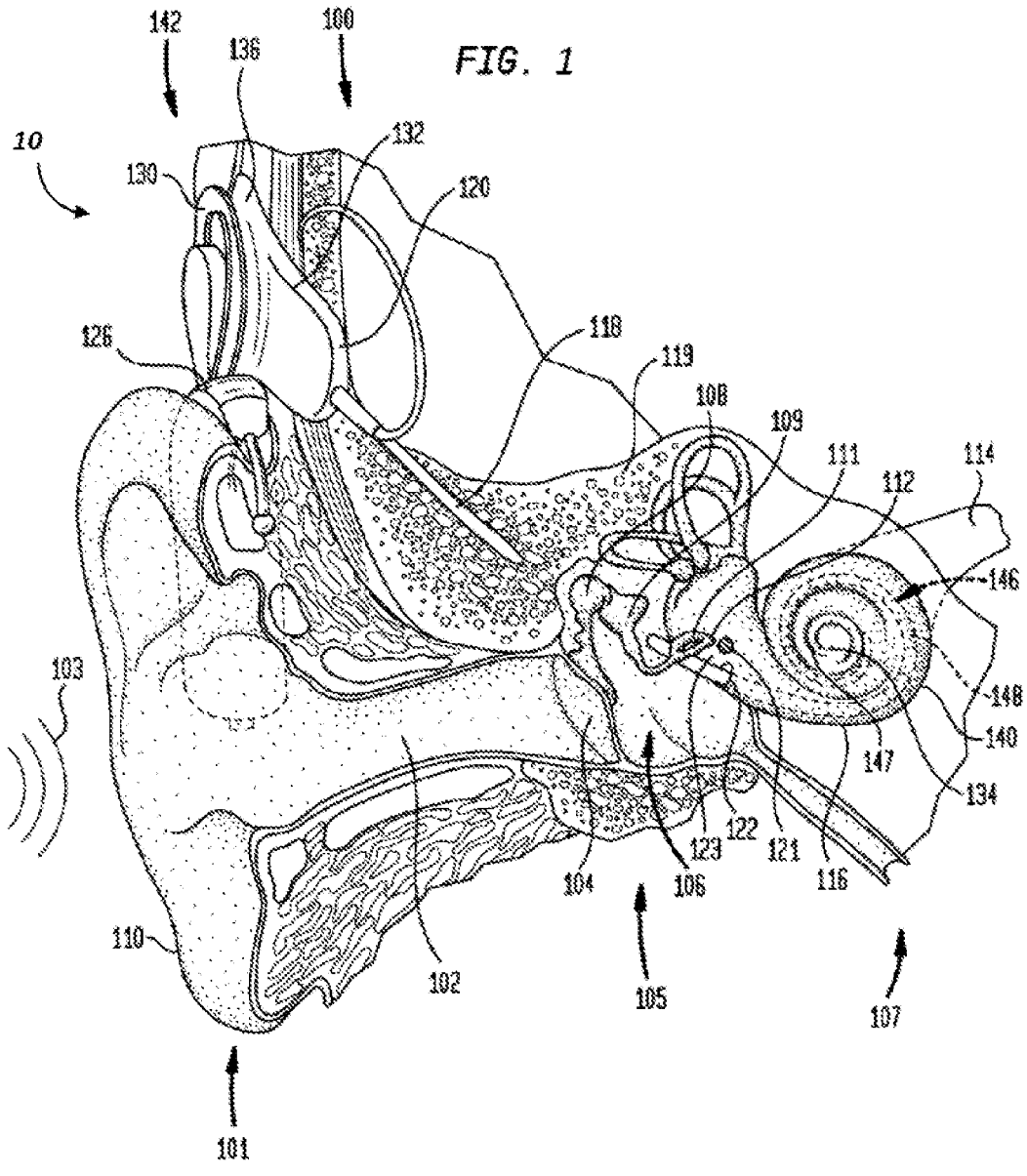
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. Additionally, it is noted that the teachings detailed herein are also applicable to other types of hearing prostheses, such as by way of example only and not by way of limitation, bone conduction devices (percutaneous, active transcutaneous and/or passive transcutaneous), direct acoustic cochlear stimulators, middle ear implants, and conventional hearing aids, etc. Indeed, it is noted that the teachings detailed herein are also applicable to so-called multi-mode devices. In an exemplary embodiment, these multi-mode devices apply both electrical stimulation and acoustic stimulation to the recipient. In an exemplary embodiment, these multi-mode devices evoke a hearing percept via electrical hearing and bone conduction hearing. Accordingly, any disclosure herein with regard to one of these types of hearing prostheses corresponds to a disclosure of another of these types of hearing prostheses or any medical device for that matter, unless otherwise specified, or unless the disclosure thereof is incompatible with a given device based on the current state of technology. Thus, the teachings detailed herein are applicable, in at least some embodiments, to partially implantable and/or totally implantable medical devices that provide a wide range of therapeutic benefits to recipients, patients, or other users, including hearing implants having an implanted microphone, auditory brain stimulators, visual prostheses (e.g., bionic eyes), sensors, etc.

In view of the above, it is to be understood that at least some embodiments detailed herein and/or variations thereof are directed towards a body-worn sensory supplement medical device (e.g., the hearing prosthesis of FIG. 1, which supplements the hearing sense, even in instances when there are no natural hearing capabilities, for example, due to degeneration of previous natural hearing capability or to the lack of any natural hearing capability, for example, from birth). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities and to recipients having no natural vision capabilities). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired, or indeed never existed. Embodiments can include utilizing the teachings herein with a cochlear implant, a middle ear implant, a bone conduction device (percutaneous, passive transcutaneous and/or active transcutaneous), or a conventional hearing aid, etc.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to implant, where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 2A:
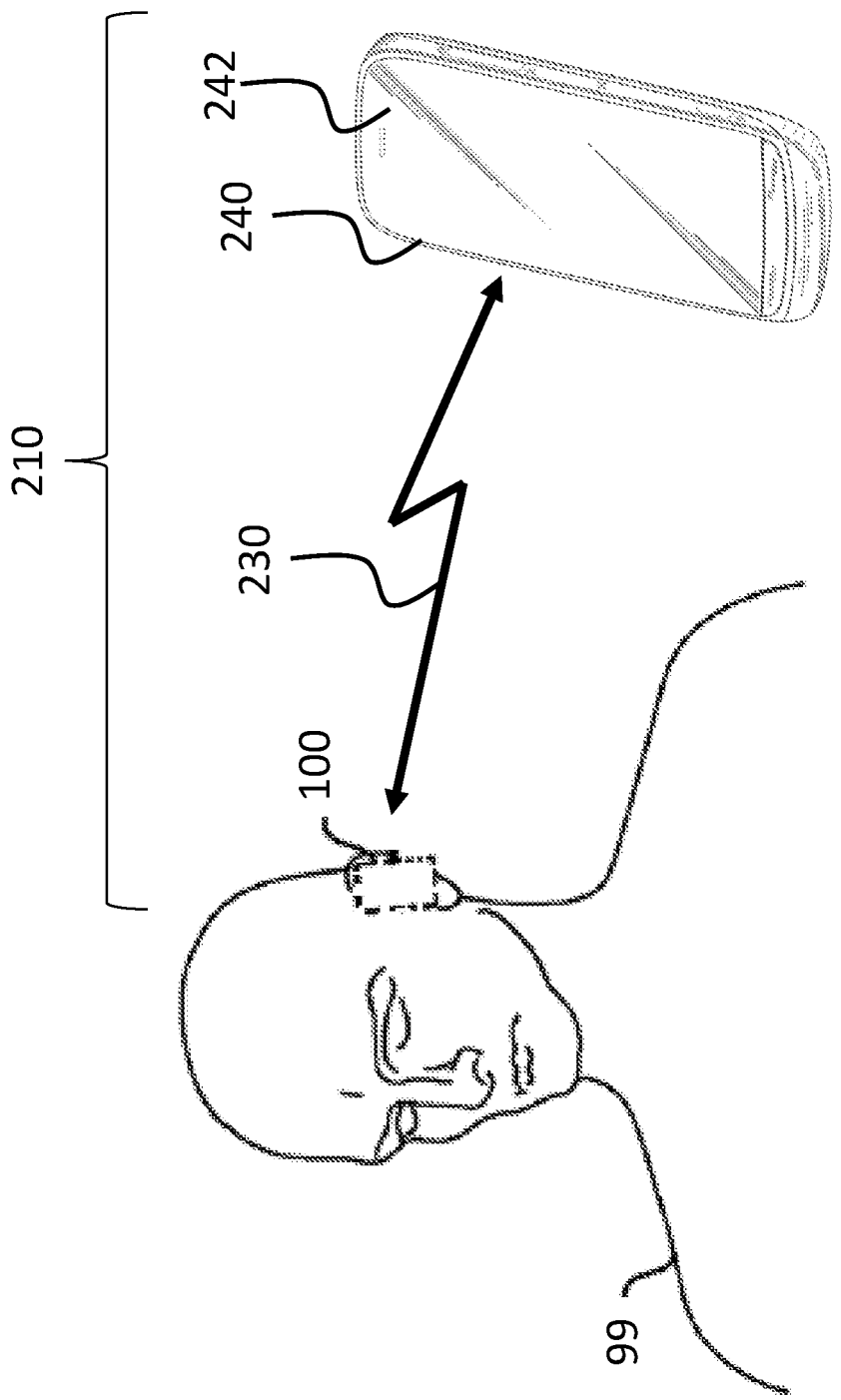
FIGS. 2A-2B presents exemplary systems.

FIG. 2A depicts an exemplary system 210 according to an exemplary embodiment, including hearing prosthesis 100, which, in an exemplary embodiment, corresponds to cochlear implant 100 detailed above, and a portable body carried device (e.g. a portable handheld device as seen in FIG. 2A, a watch, a pocket device, etc.) 240 in the form of a mobile computer having a display 242. The system includes a wireless link 230 between the portable handheld device 240 and the hearing prosthesis 100. In an embodiment, the prosthesis 100 is an implant implanted in recipient 99 (as represented functionally by the dashed lines of box 100 in FIG. 2A).

In an exemplary embodiment, the system 210 is configured such that the hearing prosthesis 100 and the portable handheld device 240 have a symbiotic relationship. In an exemplary embodiment, the symbiotic relationship is the ability to display data relating to, and, in at least some instances, the ability to control, one or more functionalities of the hearing prosthesis 100. In an exemplary embodiment, this can be achieved via the ability of the handheld device 240 to receive data from the hearing prosthesis 100 via the wireless link 230 (although in other exemplary embodiments, other types of links, such as by way of example, a wired link, can be utilized). As will also be detailed below, this can be achieved via communication with a geographically remote device in communication with the hearing prosthesis 100 and/or the portable handheld device 240 via link, such as by way of example only and not by way of limitation, an Internet connection or a cell phone connection. In some such exemplary embodiments, the system 210 can further include the geographically remote apparatus as well. Again, additional examples of this will be described in greater detail below.

As noted above, in an exemplary embodiment, the portable handheld device 240 comprises a mobile computer and a display 242. In an exemplary embodiment, the display 242 is a touchscreen display. In an exemplary embodiment, the portable handheld device 240 also has the functionality of a portable cellular telephone. In this regard, device 240 can be, by way of example only and not by way of limitation, a smart phone as that phrase is utilized generically. That is, in an exemplary embodiment, portable handheld device 240 comprises a smart phone, again as that term is utilized generically.

It is noted that in some other embodiments, the device 240 need not be a computer device, etc. It can be a lower tech recorder, or any device that can enable the teachings herein.

In an exemplary embodiment, device 240 can execute or otherwise be utilized for processing purposes associated with the prosthesis 100, such as processing captured sound, and the processed results are then conveyed to the prosthesis via link 230, where the prosthesis uses those results to evoke a hearing percept.

The phrase "mobile computer" entails a device configured to enable human-computer interaction, where the computer is expected to be transported away from a stationary location during normal use. Again, in an exemplary embodiment, the portable handheld device 240 is a smart phone as that term is generically utilized. However, in other embodiments, less sophisticated (or more sophisticated) mobile computing devices can be utilized to implement the teachings detailed herein and/or variations thereof. Any device, system, and/or method that can enable the teachings detailed herein and/or variations thereof to be practiced can be utilized in at least some embodiments. (As will be detailed below, in some instances, device 240 is not a mobile computer, but instead a remote device (remote from the hearing prosthesis 100. Some of these embodiments will be described below).)

In an exemplary embodiment, the portable handheld device 240 is configured to receive data from a hearing prosthesis and present an interface display on the display from among a plurality of different interface displays based on the received data. Exemplary embodiments will sometimes be described in terms of data received from the hearing prosthesis 100. However, it is noted that any disclosure that is also applicable to data sent to the hearing prostheses from the handheld device 240 is also encompassed by such disclosure, unless otherwise specified or otherwise incompatible with the pertinent technology (and vice versa).

It is noted that in some embodiments, the system 210 is configured such that cochlear implant 100 and the portable device 240 have a relationship. By way of example only and not by way of limitation, in an exemplary embodiment, the relationship is the ability of the device 240 to serve as a remote microphone for the prosthesis 100 via the wireless link 230. Thus, device 240 can be a remote mic. That said, in an alternate embodiment, the device 240 is a stand-alone recording/sound capture device.

It is noted that in at least some exemplary embodiments, the device 240 corresponds to an Apple Watch™ Series 1 or Series 2, as is available in the United States of America for commercial purchase as of Jun. 6, 2018. In an exemplary embodiment, the device 240 corresponds to a Samsung Galaxy Gear™ Gear 2, as is available in the United States of America for commercial purchase as of Jun. 6, 2018. The device is programmed and configured to communicate with the prosthesis and/or to function to enable the teachings detailed herein.

Figure 2B:
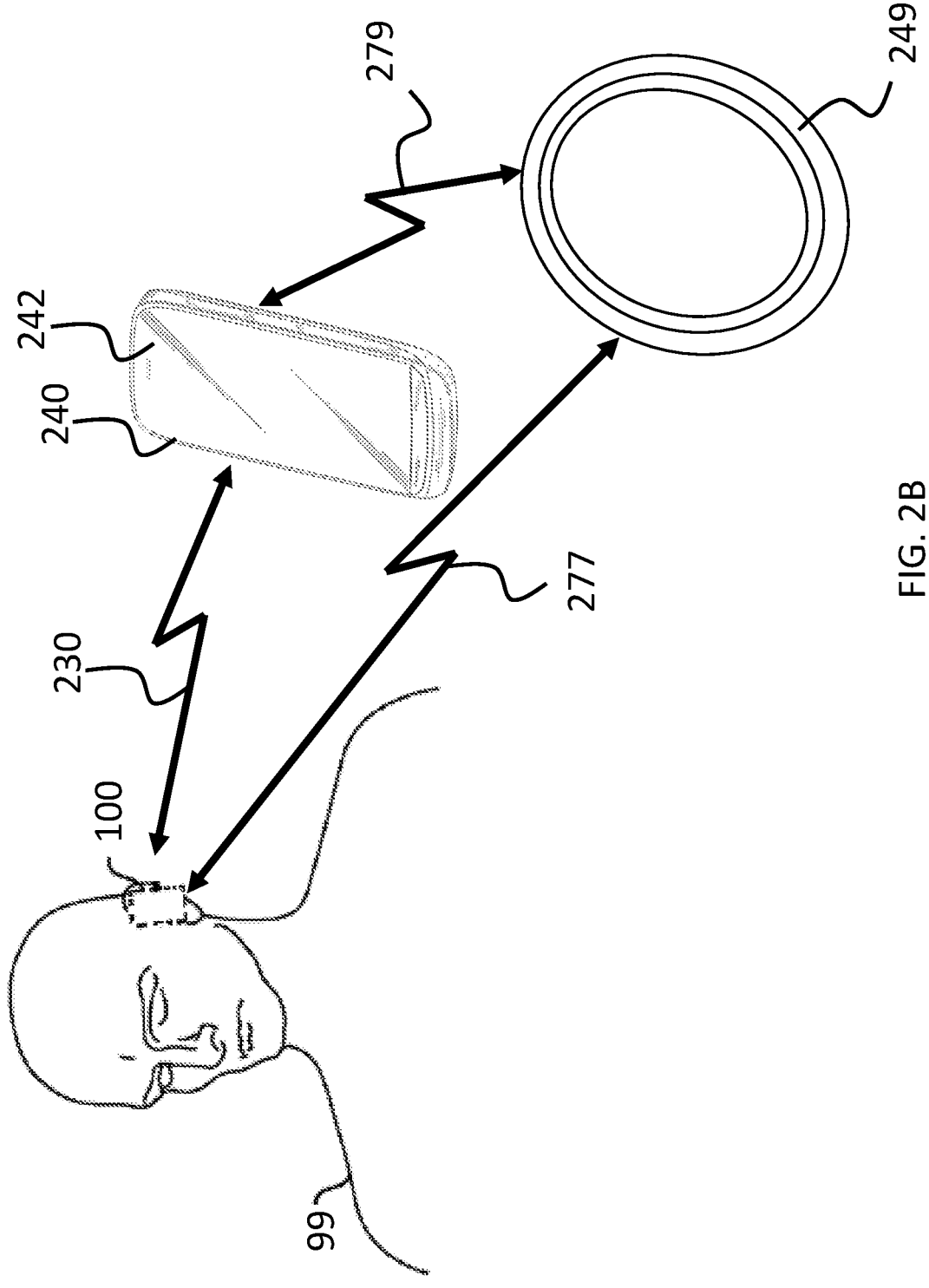

In an exemplary embodiment, a telecommunication infrastructure can be in communication with the hearing prosthesis 100 and/or the device 240. By way of example only and not by way of limitation, a telecoil 249 or some other communication system (Bluetooth, etc.) is used to communicate with the prosthesis and/or the remote device. FIG. 2B depicts an exemplary quasi-functional schematic depicting communication between an external communication system 249 (e.g., a telecoil), and the hearing prosthesis 100 and/or the handheld device 240 by way of links 277 and 279, respectively (note that FIG. 2B depicts two-way communication between the hearing prosthesis 100 and the external audio source 249, and between the handheld device and the external audio source 249—in alternate embodiments, the communication is only one way (e.g., from the external audio source 249 to the respective device)).

At least some exemplary embodiments according to the teachings detailed herein utilize advanced learning signal processing techniques, which are able to be trained or otherwise are trained to detect higher order, and/or non-linear statistical properties of signals. An exemplary signal processing technique is the so called deep neural network (DNN). At least some exemplary embodiments utilize a DNN (or any other advanced learning signal processing technique) to process a signal representative of captured sound, which processed signal is utilized to evoke a hearing percept. At least some exemplary embodiments entail training signal processing algorithms to process signals indicative of captured sound. That is, some exemplary methods utilize learning algorithms or regimes or systems such as DNNs or any other system that can have utilitarian value where that would otherwise enable the teachings detailed herein to analyze captured sound. It is noted that the aforementioned discussion focused on sound. It is noted that the teachings detailed herein can also be applicable to captured light. In this regard, the teachings detailed herein can be utilized to analyze or otherwise process a signal that is based on captured light, and evoke a sensory percept, such as a vision percept, based on the processed signal.

A "neural network" is a specific type of machine learning system. Any disclosure herein of the species "neural network" constitutes a disclosure of the genus of a "machine learning system." While embodiments herein focus on the species of a neural network, it is noted that other embodiments can utilize other species of machine learning systems accordingly, any disclosure herein of a neural network constitutes a disclosure of any other species of machine learning system that can enable the teachings detailed herein and variations thereof. To be clear, at least some embodiments according to the teachings detailed herein are embodiments that have the ability to learn without being explicitly programmed. Accordingly, with respect to some embodiments, any disclosure herein of a device or system constitutes a disclosure of a device and/or system that has the ability to learn without being explicitly programmed, and any disclosure of a method constitutes actions that results in learning without being explicitly programmed for such.

Some of the specifics of the DNN utilized in some embodiments will be described below, including some exemplary processes to train such DNN. First, however, some of the exemplary methods of utilizing such a DNN (or any other system that can have utilitarian value) will be described.

It is noted that in at least some exemplary embodiments, the DNN or the product from machine learning, etc., is utilized to achieve a given functionality as detailed herein. In some instances, for purposes of linguistic economy, there will be disclosure of a device and/or a system that executes an action or the like, and in some instances structure that results in that action or enables the action to be executed. Any method action detailed herein or any functionality detailed herein or any structure that has functionality as disclosed herein corresponds to a disclosure in an alternate embodiment of a DNN or product from machine learning, etc., that when used, results in that functionality, unless otherwise noted or unless the art does not enable such.

Figure 3:
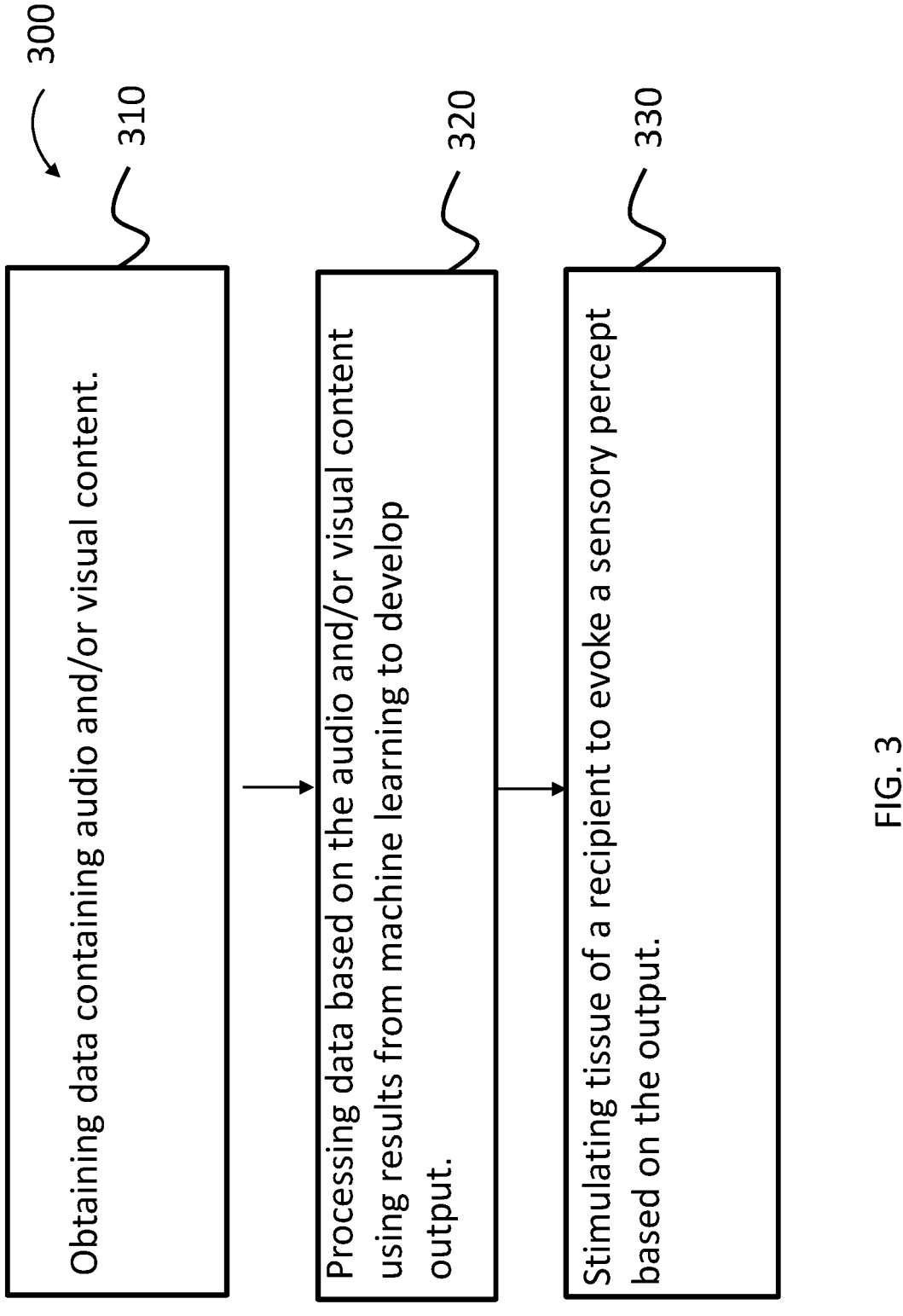
FIG. 3 presents an exemplary flowchart for an exemplary method.

FIG. 3 depicts an exemplary flowchart for an exemplary method, method 300, of utilizing a product of and/or from machine learning, such as a DNN, according to an exemplary embodiment. Method 300 includes method action 310, which includes obtaining data based on audio and/or visual content. In an exemplary embodiment, the obtained data is a signal containing audio and/or video content. In an exemplary embodiment, this is the signal that comes from the sound capture device of the prosthesis, such as the microphone. In an exemplary embodiment, this is the signal that comes from a digital and/or analog device, such as an MP3 player, that contains the sound. Alternatively, and/or in addition to this, this is the signal that is streamed from a television or the like utilizing Wi-Fi or some form of wireless system, which signal is received by the prosthesis. With respect to the future associated with visual content, this can come from the light capture device of a retinal implant, and/or could come from a device such as an analog and/or digital device that provides a signal to the prostheses in an analog and/or digital form.

Method 300 further includes method action 320, which includes processing data based on the audio and/or visual content using a product or results from machine learning to develop output. In an exemplary embodiment, this can correspond to processing the raw signal from the microphone, and thus the data based on the audio and/or visual content is the data that is obtained in method action 310. Further, this action of method action 320 can correspond to processing a modified signal or even a new signal that is ultimately based on the signal from the microphone. In an exemplary embodiment, the action of processing can occur after the filtering or the like of a signal obtained from the microphone is executed. In an exemplary embodiment, the product is a chip that is fabricated based on the results of machine learning. In an exemplary embodiment, the product is a neural network, such as a deep neural network (DNN). The product can be based on or be from a neural network. In an exemplary embodiment, the product is code. In an exemplary embodiment, the product is a logic circuit that is fabricated based on the results of machine learning. The product can be an ASIC (e.g., an artificial intelligence ASIC). The product can be implemented directly on a silicon structure or the like. Any device, system and or method that can enable the results of artificial intelligence to be utilized in accordance with the teachings detailed herein, such as in a hearing prosthesis or a component that is in communication with a hearing prosthesis, can be utilized in at least some exemplary embodiments. Indeed, as will be detailed below, in at least some exemplary embodiments, the teachings detailed herein utilize knowledge/information from an artificial intelligence system or otherwise from a machine learning system.

Exemplary embodiments include utilizing a trained neural network to implement or otherwise execute at least one or more of the method actions detailed herein, and thus embodiments include a trained neural network configured to do so. Exemplary embodiments also utilize the knowledge of a trained neural network/the information obtained from the implementation of a trained neural network to implement or otherwise execute at least one or more of the method actions detailed herein, and accordingly, embodiments include devices, systems and/or methods that are configured to utilize such knowledge. In some embodiments, these devices can be processors and/or chips that are configured utilizing the knowledge. In some embodiments, the devices and systems herein include devices that include knowledge imprinted or otherwise taught to a neural network. The teachings detailed herein include utilizing machine learning methodologies and the like to establish sensory prosthetic devices or supplemental components utilized with sensory prostatic devices (e.g., a smart phone), to replace or otherwise augment the processing functions, etc. (e.g., sound or light processing, etc.) of a given sensory prostheses.

As noted above, method action 320 entails processing the data utilizing a product of machine learning, such as the results of the utilization of a DNN, a machine learning algorithm or system, or any artificial intelligence system that can be utilized to enable the teachings detailed herein. This as contrasted from, for example, processing the data utilizing general code or utilizing code that not from a machine learning algorithm or utilizing a non AI based/resulting chip, etc. In an exemplary embodiment, a typical cochlear implant processes a signal from a microphone and subsequently provides the results of that processing to a stimulation device that stimulates various electrodes in a weighed manner. This processing is typically done by a sound processor which includes filter banks that simply divides up an input signal into separate filter groups or filter bins. This is not the utilization of a machine learning algorithm. That said, it is noted that in some embodiments, this division can be executed utilizing results from machine learning (e.g., a trained DNN, on whatever medium that can enable such, such as a chip).

Again, in an exemplary embodiment, the machine learning can be a DNN, and the product can correspond to a trained DNN and/or can be a product based on or from the DNN (more on this below).

FIG. 3 further includes method action 330, which includes stimulating tissue of a recipient to evoke a sensory percept based on the output that is developed in method action 320. In an exemplary embodiment where method 300 is executed utilizing a cochlear implant, the sensory percept is a hearing percept (or where method 300 is executed in part utilizing a cochlear implant—in an exemplary embodiment, method action 310 and/or method action 320 can be executed by a separate device, such as by way of example only and not by way of limitation, device 240, and/or a remote device or the like, such as a device that is in communication with the tele-coil). Thus, in an exemplary embodiment where method 300 is executed utilizing a cochlear implant, the data obtained in method action 310 contains at least audio content. In an exemplary embodiment where method 300 is executed utilizing a retinal prosthesis or the like, method action 330 results in a visual percept, and thus, in an exemplary embodiment, the data obtained in method action 310 contains at least visual content.

Consistent with the teachings detailed above, in an exemplary embodiment, all of the actions associated with method 300 are executed by a self-contained body worn sensory prosthesis. Still, in other embodiments, such as where processing power is constrained, some of the actions are executed by device that is separate from the self-contained body worn sensory prosthesis, and the results of those actions are communicated to the sensory prosthesis so that the sensory prosthesis can evoke a sensory percept based on the results of that action.

Figure 4:
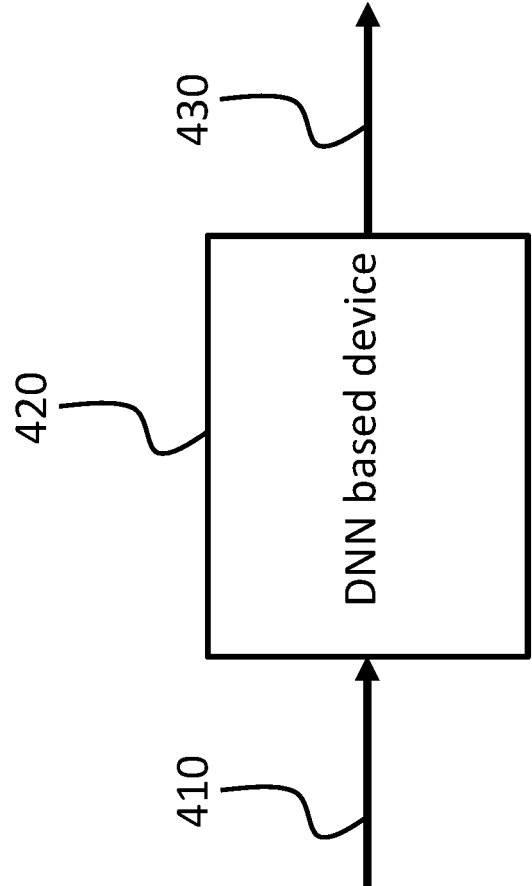
FIG. 4 presents an exemplary functional diagram for an exemplary embodiment.

FIG. 4 depicts an exemplary conceptual functional black box schematic associated with method action 320, where a sound signal 410 is the input into a DNN based device 420 that utilizes a trained DNN or some other trained learning algorithm or trained learning system (or the results thereof—in an exemplary embodiment, the product of—machine learning—as used herein can correspond to a trained learning algorithm or trained learning system as used in operational mode after training has ceased and product of machine learning can correspond to a product that is developed as a result of training—again, this will be described in greater detail below), and the output is a signal 430 that is provided to a stimulation device of the prosthesis that evokes a sensory percept. In this exemplary embodiment, device 420 can be a sound processor or a light processor of a hearing or vision prostheses, respectively, albeit unique and novel sound processors and light processors.

It is noted that in at least some exemplary embodiments, the input 410 comes directly from a microphone, while in other embodiments, this is not the case. Input 410 can correspond to any input that can enable the teachings detailed herein to be practiced providing that the art enables such. Thus, in some embodiments, there is no "raw sound" input into the DNN. Instead, it is all pre-processed data. Any data that can enable the DNN or other machine learning algorithm or system to operate can be utilized in at least some exemplary embodiments.

Some additional features of the device 420 are described below as utilized in a cochlear implant, but for now, it is noted that at least some embodiments can include methods, devices, and/or systems that utilize a DNN inside a cochlear implant system and/or along with such a system for the analysis of sound and/or the generation of electrical stimulation patterns to be applied inside the cochlea. In some embodiments, a neural network, such as a DNN, is used to directly interface to the audio signal coming from one or more microphones, process this audio data via its neural net, and determine the locations and strengths of electrical stimuli inside the cochlea. The network can be, in some embodiments, either a standard pre-trained network where weights have been previously determined (e.g., optimized) and loaded onto the network, or alternatively, the network can be initially a standard network, but is then trained to improve specific recipient results based on outcome oriented reinforcement learning techniques.

In some embodiments, the network will interface to conventional cochlear implant sound processing at the point of mapping to the recipients pre-determined psychophysical threshold and comfort levels. Thus, in some exemplary embodiments, the output of the neural network will be an electrode channel specific stimulation pattern with given electrode channel energies which are then mapped within the dynamic range of the recipients hearing bandwidth for those electrode channel.

Briefly, it is noted that "electrode channels" refer to the electrodes, as opposed to frequency bins. The art sometimes refers to channels as the frequency bins, where the number of electrode channels equals the number of bins. Here, the bins outnumber the electrode channels. Sometimes, the phrase channels is used herein to refer to traditional frequency bins.

Returning back to method 300, in some embodiments, method action 320 is executed by processing audio in neural network sound processing applications. In an exemplary embodiment, method action 310 and/or an action intervening between method action 310 and method action 320 can include preparing the audio data for the neural network by digitizing the analog audio signal into a digital audio signal, and then transforming the time domain audio signal into the frequency domain (typically using a short time Fourier transform—STFT). The number of frequency bins to use in the STFT can depend, in some embodiments, on the amount of processing power available and the accuracy demands of the application.

It is noted that some embodiments include utilizing the neural network itself to perform this time to frequency transformation. In other embodiments, traditional filter methods and devices are utilized to execute this task, and this task is specifically excluded from the actions of the neural network.

Figure 5:
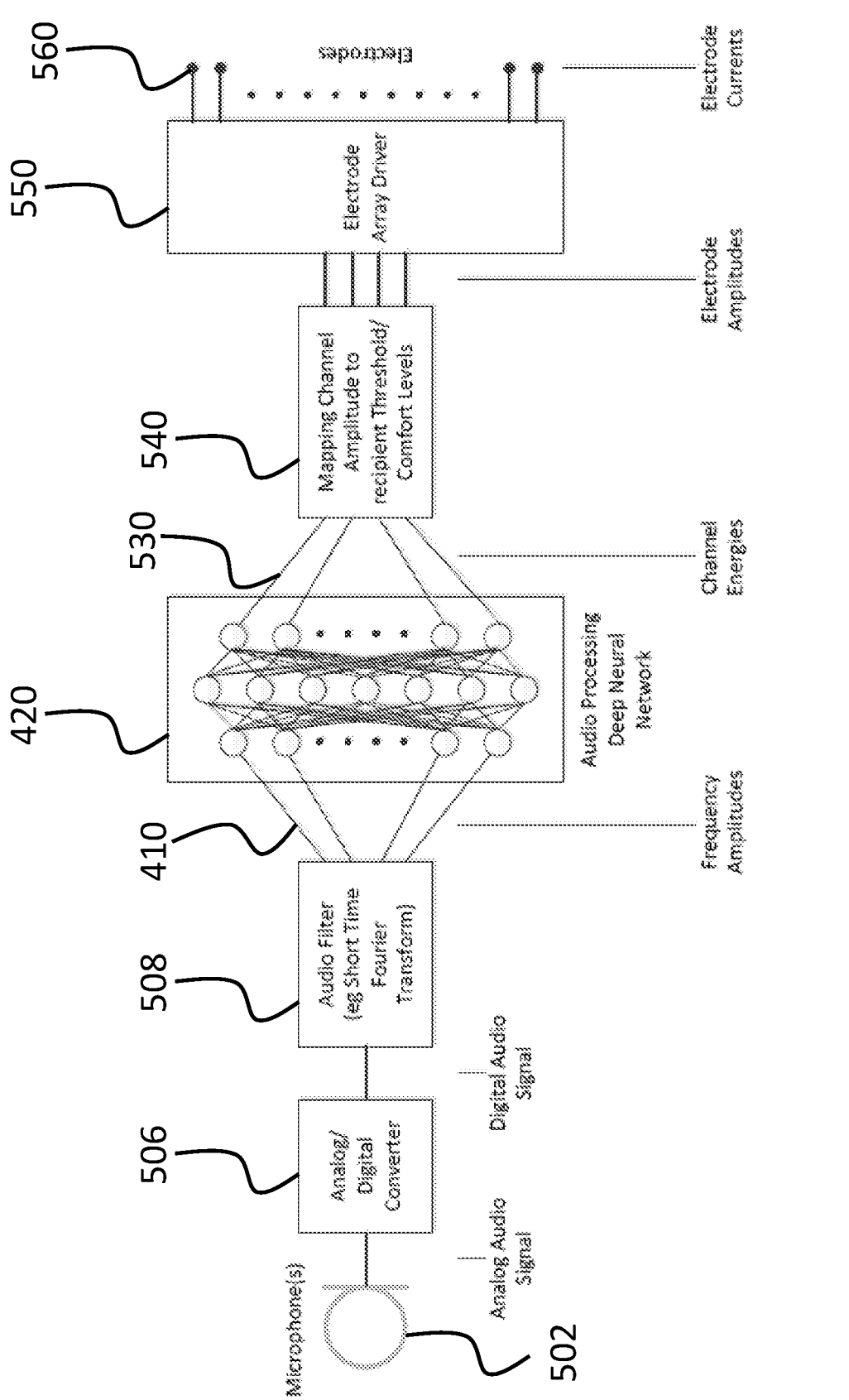
FIG. 5 presents another exemplary functional diagram for an exemplary embodiment.

FIG. 5 presents an exemplary system for executing method 300. As seen, microphone 502, which can correspond to the microphone of the hearing prosthesis presented in FIG. 1, can execute method action 310. Upstream processing component 506 converts the analog signal captured by the microphone into a digital signal. Thus, collectively, microphone 502 and converter 506 can execute method action 310. As seen, there is an audio filter 508 that can break up the now digitized signal in two different filter bins or otherwise establish different signals for respective frequencies, where the output of filter 508 corresponds to input 410 into device 420 in an exemplary embodiment.

The frequency amplitudes from filter 508 are then fed into the neural network inputs so as to be obtained by device 420. In at least some exemplary embodiments, the network will have already been loaded with pre-taught weights (more on this below). The neural network of device 420 then determines the electrode channel energies that can be utilitarianly stimulated based on the audio input, and then feeds this data to the recipient threshold/comfort level mapping section 540. Mapping section 540 produces electrode amplitudes which are then converted to electrode currents in the electrode array driver 550.

In an exemplary embodiment, device 420 is a microprocessor or otherwise a system that includes the product from the machine learning. In an exemplary embodiment, mapping section 540 constitutes circuitry that may include logic circuits that receives the output from the processor 420 and applies weights to the outputs associated with the recipient threshold and/or comfort levels. In this regard, mapping section 540 can correspond to a processor of a cochlear implant. Indeed, in an exemplary embodiment, a cochlear implant can be obtained, and device 420 can be inserted in between the audio filter 508 and the mapping section 540. It is noted that in some embodiments, element 508 and 540 can be part of a single processor. Accordingly, in an exemplary embodiment, the processor could be modified to include the features associated with device 420, or otherwise can include a separate processor that communicates with the processor of the cochlear implant/the cochlear implant sound processor, to execute the actions associated with device 420. (It is noted that in an alternate embodiment, processor 420 is replaced with a non-processing device, or includes non-processing devices, such as a chip or the like that is a result of a machine learning algorithm or machine learning system, etc. Any disclosure herein of a processor corresponds to a disclosure in an embodiment of a non-processor device or a combined processor-non-processor device where the non-processor is a result of machine learning.)

In an exemplary embodiment, device 420 and device 540 are all part of a single processor. In an exemplary embodiment, device 508, device 420, and device 540 are all part of a single processor. Thus, in an exemplary embodiment, there is a processor that is programmed and configured or otherwise contains code or circuitry or switches, etc., to execute one or more of the functionalities detailed herein associated with elements 508, 420, and 540. Further, in an exemplary embodiment, this processor can include or otherwise be configured to execute the functions of the converter 506.

In an exemplary embodiment, the aforementioned processor is a general-purpose processor that is configured to execute one or more the functionalities herein. Again, in some embodiments, the processor includes a chip that is based on machine learning/from machine learning. In an exemplary embodiment, the aforementioned processor is a modified cochlear implant sound processor that has been modified to execute one or more of the functionalities detailed herein, such as via the inclusion of an ASIC developed as a result of machine learning. In an exemplary embodiment, a solid-state circuit is configured to execute one or more of the functionalities detailed herein. Any device, system, and/or method that can enable the teachings detailed herein can be utilized in at least some exemplary embodiments.

It is noted that in an exemplary embodiment, the device 420 can reside or otherwise be on the smart device 240 detailed above. In an exemplary embodiment, the processor of the smart device can have the functionality via programming or the like of device 420. In an exemplary embodiment, the microphone of the smart device corresponds to microphone 502, and the processing chain all the way to the output 530 and/or the output of section 540 can be executed by the smart device 240. Thus, in an exemplary embodiment, there is a smart device that is configured to execute one or more the functionalities associated with these components. In an exemplary embodiment, the smart device can indicate via a link with the hearing prosthesis to provide the output of the map section 540 to the prostheses, and the prostheses utilizes that output to evoke a hearing percept.

Returning back to method 300, in an exemplary embodiment, at least some of the method actions associated with method 300 are executed utilizing a hearing prosthesis. The following embodiments will now be described in terms of such, and thus in an exemplary embodiment of the method 300, method action 310 contains audio content, and the evoked sensory percept evoked in method action 330 is a hearing percept.

Figure 6:
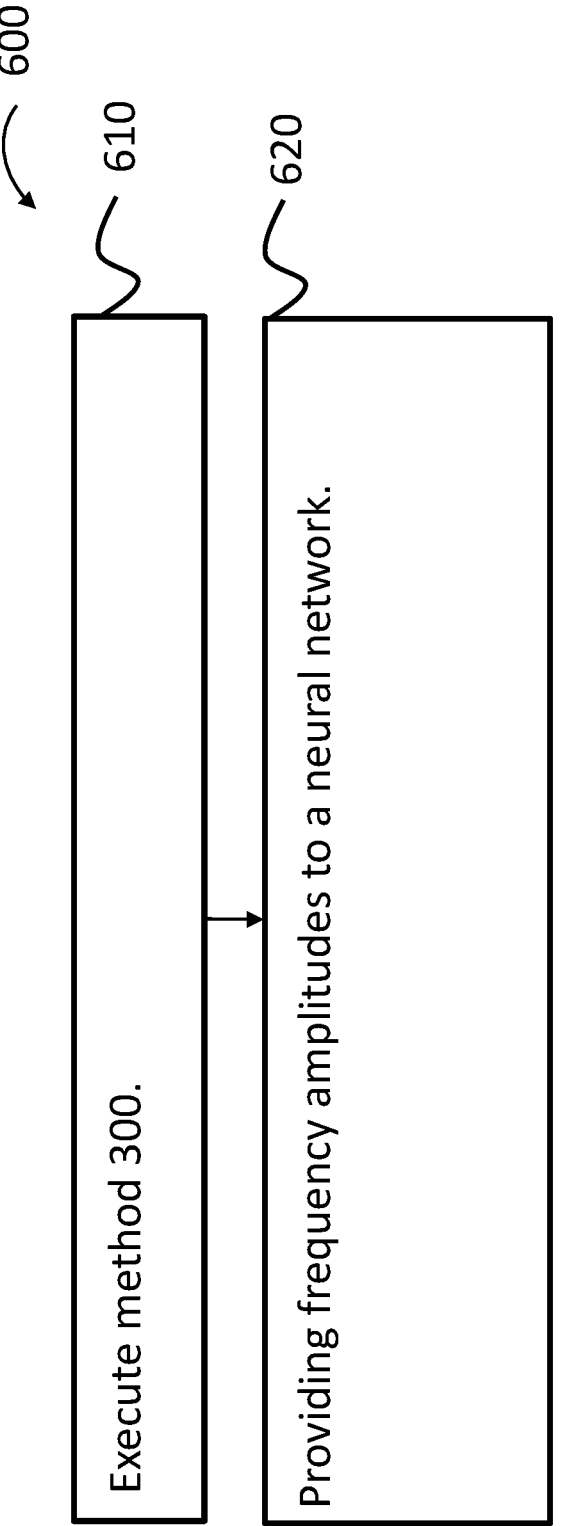
FIG. 6 presents another exemplary flowchart for an exemplary method.

Further, as noted above, in an exemplary embodiment, the product that is utilized to execute method action 320 can be a product that is at least part of a neural network. In this regard, now with reference to FIG. 6, which presents an exemplary flowchart for an exemplary algorithm for an exemplary method, method 600, which includes method action 610, which includes executing method 300. Method 600 also includes method action 620, which includes providing frequency amplitudes to the neural network (e.g., the device 420).

By way of example only and not by way of limitation, in an exemplary embodiment, this can entail providing the output signals of the various filter bins to device 420. In an exemplary embodiment, the filtering does not change or otherwise adjust the amplitudes of the signals. In an alternative embodiment, the output of the filters is data that includes frequency information and/or amplitude information, and this information is utilized by the device 420. Any device, system, and/or method that can enable device 420 to be provided with the pertinent data to implement the teachings detailed herein utilizing the DNN and can be utilized in at least some exemplary embodiments.

In an exemplary embodiment of method 600, the action of analyzing data includes determining electrode channel energies for a cochlear implant having components that are implanted in a person that are to be stimulated based on the provided frequency amplitudes. Further, the stimulation of the tissue is executed using the cochlear implant.

Thus, as can be seen, in an exemplary embodiment, there is a device comprising a sensory prosthesis, such as a hearing prosthesis. The hearing prosthesis includes an input subsystem configured to receive input based on sound (e.g., a microphone, a WIFI device configured to receive streamed audio signals, etc.) and an output subsystem configured to stimulate tissue (e.g., the electrode array, a mechanical actuator that imparts vibration to tissue, etc.), based on input into the input subsystem to evoke a hearing percept. In an exemplary embodiment, a neural network interposed between the input subsystem and the output subsystem. In an exemplary embodiment, the neural network is part of an output side processing arrangement of an audio processing system of the hearing prosthesis. That said, in an exemplary embodiment, the neural network can also be part of the input side processing arrangement of an audio processing system of the hearing prosthesis.

Accordingly, in an exemplary embodiment, the neural network automatically determines electrode channel energies to be stimulated based on input received by the input subsystem and provides the determined electrode channel energies downstream for ultimate utilization by the output subsystem to evoke a hearing percept.

It is noted that in some embodiments, section 540 adjusts the received input from device 420 to accommodate or otherwise meet recipient threshold and/or comfort levels. By way of example only and not by way of limitation, for a given electrode channel, which results in the application of electrical energy at a given location within a cochlea, a recipient has a threshold level and a comfort level, or more specifically, the prosthesis has a mapped threshold level and a comfort level for that electrode channel. The prosthesis will adjust the input energy to accommodate those levels. For example, if the input energy has a very high level of energy, the prosthesis might lower the amount of energy so that it does not exceed a comfort level for that electrode channel, whereas for another electrode channel, the comfort level might be higher, and thus the prosthesis would not necessarily lower the amount of energy for that electrode channel. Put another way, because the output of the DNN is not electrode channel specific or otherwise not static with respect to which electrode channels will be utilized for given frequencies, a given frequency will be applied to a recipient but constrained by different and/or threshold levels for a electrode channel relative to another electrode channel. In an exemplary embodiment, section 540 performs the adjustment/mapping, while in other embodiments, the DNN can execute the adjustment/mapping, or otherwise can be built into the product.

Figure 7:
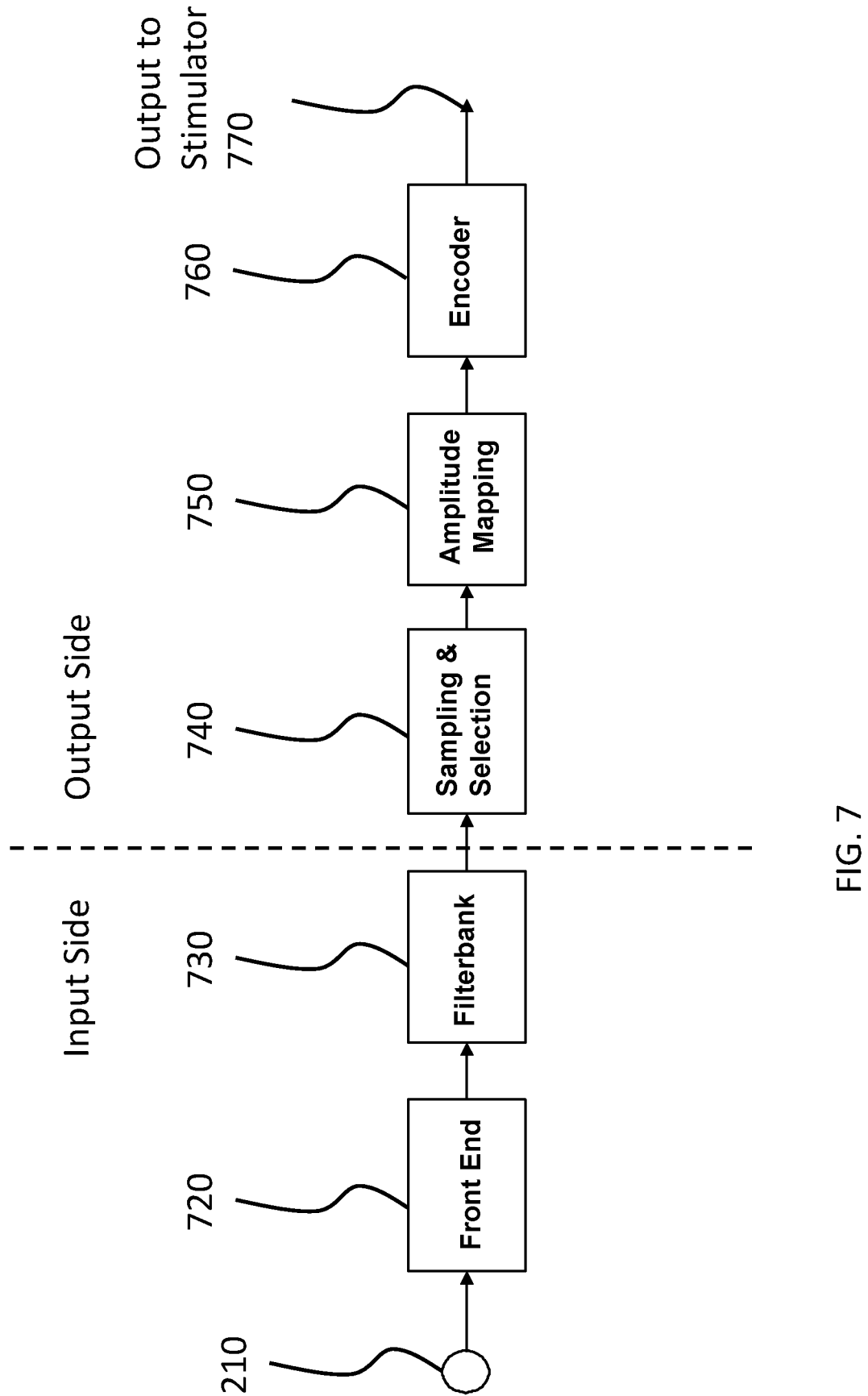
FIG. 7 presents an exemplary functional diagram for an exemplary embodiment.

FIG. 7 presents an exemplary high level functional schematic of an exemplary embodiment, with emphasis on an overall signal processing scheme utilized in at least some embodiments. As can be seen, a stimulus capture device 702, which can correspond to an image sensor, such as a digital image sensor (e.g., CCD, CMOS), or a sound sensor, such as a microphone, etc. The transducer of device 702 outputs a signal to the components of the so-called front end 720, which amplifies and combines the signals from device 710, and, in some embodiments, can incorporate automatic gain control (AGC). In an exemplary embodiment, component of the front-end can include amplifiers, and/or prefilters, etc.

Output from the front end 720 is provided to a filter bank 730, which splits the light or sound, depending on the embodiment, into multiple frequency bands. With respect to embodiments directed towards hearing prostheses, the splitting emulates the behavior of the cochlea in a normal ear, where different locations along the length of the cochlea are sensitive to different frequencies. In at least some exemplary embodiments, the envelope of each filter output controls the amplitude of the stimulation pulses delivered to a corresponding electrode. With respect to hearing prostheses, electrodes positioned at the basal end of the cochlea (closer to the middle ear) are driven by the high frequency bands, and electrodes at the apical end are driven by low frequencies. In at least some exemplary embodiments, the outputs of filter bank 730 are a set of signal amplitudes per electrode channel or plurality of electrode channels, where the electrode channels are respectively divided into corresponding frequency bands.

As can be seen in FIG. 7, the functional schematic has been divided into an input side and an output side. Accordingly, various references will be made to "input stages" and "output stages." As used herein, input stages have at least the following functionalities: management of the input, such as the utilization of feedback elimination algorithms where a portion of the signal coming from capture device 710 is canceled and data signal cancellation, where again, a portion of the signal from capture device 710 is canceled. In an exemplary embodiment, the aforementioned canceling can be utilized to achieve noise reduction, and therefore, such cancellation that occurs on the input side corresponds to an input stage operation. Speech enhancement and beamforming/directional sound capture techniques are also input side processes. Of course, as noted above, the prefiltering and the filtering of filter bank 730 also entail the management of the input. The utilization of signal/data compression, etc., so as to enable the sampling and selection block 740 to perform in a more efficient manner and/or in a power conservancy mode is also included in the input side signal management.

The sampling and selection block 740 (on the output side) samples the output of the filter bank 730, such as the filter bank envelopes, and determines the timing and pattern of the stimulation on each electrode. In general terms, sampling and selection block 740 selects certain electrode channels as a basis for stimulation, based on the amplitude and/or other factors. Still in general terms, sampling and selection block 740 determines how stimulation will be based on the channels corresponding to the divisions established by the filter bank 730. In at least some exemplary embodiments, the actions of the sampling and selection block are executed by a so-called sound processor with respect to a hearing prosthesis. In an exemplary embodiment, block 740 corresponds to device 240.

In some exemplary embodiments, stimulation rates on each electrode (electrodes of a cochlear electrode array, for example) can range from 250 to 3500 pulses per second, and embodiments include stimulation rates at any value or range of values therebetween in 1 pulse per second increments (e.g., 350 pulses per second, 3333 pulses per second, 355 to 941 pulses per second, etc.). In some other exemplary embodiments, stimulation rates on each electrode (electrodes of a retinal electrode assembly for example) may range from 50 pulses to 2,500 pulses per second, and embodiments include stimulation rates at any value or range of values therebetween in 1 pulse per second increments. In an exemplary embodiment, the stimulation is applied in pulses having pulse widths of 10 to 25 μs duration or any value or range of values therebetween in one microsecond increments. The amplitude mapping block 750 compresses the filter bank envelopes to determine the current level of each pulse. Currents having utilitarian value can be in the range 100 to 1000 μA, or any value or range of values therebetween in 1 μA increments. Such current levels vary both amongst implant recipients and across the electrode apparatus. With respect to a hearing prosthesis, amplitude and mapping block 750 is set by a clinician, or more accurately, the algorithm that is utilized to set the current levels is set by the clinician, and the sound processor, using that algorithm, implements the amplitude of the stimulation based on that algorithm. The final block (final by way of example) is the encoder 760, which encodes the data provided from block 750, so that the data can be transmitted to the stimulator. In an exemplary embodiment, the data is encoded for the purposes of transmission over a 5 MHz inductance link via a transcutaneous transmission to an implanted stimulator, and outputted (as represented by arrow 770) to the stimulator component that stimulates the tissue of the recipient to evoke the vision and/or hearing percept.

Consistent with the notations above and below, in an exemplary embodiment, these blocks do not exist per se as identifiable blocks in the prostheses or in a component that is utilized with the prostheses. Instead, there is the product of machine learning (either directly or indirectly/based thereon), or a DNN, etc., that has the functionality associated with these blocks, and executes the functionality based on the input in view of its training. Accordingly, any disclosure of a block or the like in a functionality associated there with can correspond to a disclosure of a DNN or product from machine learning that has that functionality.

Indeed, in an exemplary embodiment, it is possible that any part of the output side processing can be replaced with the product from the machine learning and/or the DNN, etc. As is also noted, in some embodiments, the product/DNN can also implement or otherwise execute some of the input side processing functionality as well.

From the above, it can be seen that in an exemplary embodiment, the device is configured such that the neural network automatically determines electrode channel energies to be stimulated based on input received by the input subsystem and provides the determined electrode channel energies downstream for ultimate utilization by the output subsystem to evoke a hearing precept.

Some additional features of the processing chain will be described in greater detail below, along with functionalities that are executed by the DNN in some embodiments. Briefly, with respect to some higher-level functionality, in an exemplary embodiment, the neural network can have utilitarian value with respect to, in some embodiments, extracting useful sound in a noisy environment. Further, in an exemplary embodiment, the neural network can be utilized to improve or otherwise expand the dynamic range. In this regard, in an exemplary embodiment, such can have utilitarian value in scenarios where the sound input or the audio input is music, where slight variations of the input frequencies can be lost in a typical cochlear implant. Some additional details of this will be described in greater detail below with respect to method 300, or more accurately, a variation thereof, but briefly, it is noted that in an exemplary embodiment, the neural network is configured to expand a dynamic range of input on a variable manner beyond that which would be the case in the absence of the neural network. Further along these lines, in an exemplary embodiment, the neural network is configured to or otherwise to be used to differentiate between voices and/or instruments. In an exemplary embodiment, the teachings detailed herein can be utilized to provide an output to the recipient that more sounds like a female voice when the speaker is female, and more sounds like a male voice when the speaker is male. Moreover, in an exemplary embodiment, the neural network can be utilized to provide an output that enables the recipient to better differentiate between different male voices. In this regard, normal hearing people have the utilitarian ability to recognize voices, especially those close to them or otherwise voices of people with whom they spend a certain amount of time. The cochlear implant recipient may not necessarily be able to do this. By utilizing the neural network, voice differentiation may be more readily achieved relative to that which would be the case in the absence of the utilization of a neural network, such as with respect to the utilization of a standard cochlear implant sound processor that utilizes any of the strategies that are known in the prior art, such as some of the strategies that are noted below.

In this regard, it is noted that in at least some exemplary embodiments, the cochlear implant divides the input provided into the input subsystem into 22 different frequency bins, where, in at least some exemplary embodiments, the frequencies do not overlap. The processor of the cochlear implant processes the data from the frequency bins as electrode channels of the cochlear implant, and provides output to the stimulator of the cochlear implant, weighted or otherwise, in 22 different electrode channels, which electrode channels correspond to 22 different electrodes of the electrode array, and thus 22 different stimulations from the 22 different electrodes. In some alternate embodiments, the cochlear implant divides input provided into the subsystem into more than 22 different frequency bins, again where, in at least some exemplary embodiments, the frequencies do not overlap. By way of example, there can be N number of frequency bins, where N equals 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In an exemplary embodiment, N can be any integer between and including 5 to 10,000 or any range of values therebetween in 1 increment (e.g., 30, 140, 25 to 5003, etc.). Moreover, in an exemplary embodiment utilizing a DNN (although other systems that can enable such can be used), N can be any integer between and including 5 to 100,000, or 5 to 250,000 or 5 to 1,000,000 or more. In an exemplary embodiment, the stimulator of the electrode array or otherwise the output device has M number of output electrode channels, where M equals 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more or any range of values therebetween in 1 increment. In an exemplary embodiment, M can be any integer between and including 3 to 10,000 or any range of values therebetween in 1 increment (e.g., 30, 140, 25 to 5003, etc.). Moreover, in an exemplary embodiment utilizing a DNN (although other systems that can enable such can be used), M can be any integer between and including 3 to 100,000, or 3 to 250,000 or 3 to 1,000,000 or more. In some embodiments, N will be greater than M.

In an exemplary embodiment, the arrangement above can have utilitarian value with respect to activating different electrode channels of the prosthesis for the same frequencies over a temporal period where the frequencies are re-encountered. By way of example only and not by way of limitation, during normal use of the hearing prosthesis, or otherwise via the utilization of a standard cochlear implant, for example, the prosthesis may apply the frequencies 700 Hz and 720 Hz to the same electrode channel (e.g., electrode 7 of a 22 electrode array) in the same way. This can be because, in an exemplary embodiment, there are only 22 frequency bins, and a frequency bin encompasses those two frequencies. Thus, the recipient will perceive these two separate frequencies as the same frequency in at least some instances, because the same electrode is stimulated the same way. In some embodiments, there is utilitarian value with respect to the fact that the electrode channels are tonotopically mapped to the recipient's cochlea, and thus the recipient will perceive the aforementioned frequencies to be about those frequencies. However, in some alternate embodiments, such as where there is utilization of more than 22 frequency bins, the frequencies of 700 Hz could be located in a different frequency bin than the frequencies of 720 Hz. In an exemplary embodiment, the neural network could make a determination that one electrode will be stimulated for the 700 Hz, and another, separate electrode, will be stimulated for the 720 Hz, even though one of those electrodes is not the electrode that is tonotopically mapped to the recipient's cochlea. Accordingly, in this exemplary embodiment, the recipient may perceive a different frequency for one of those frequencies than that which would normally be perceived, and/or as well as that which should be perceived for normal hearing, but the recipient will also be able to understand that there are two separate frequencies that have been captured.

It is briefly noted that in the aforementioned scenario, it does not necessarily mean that simply because the two frequencies have been placed into two separate frequency bins, that those two separate frequencies will be applied to two different electrode channels. The utilization of the greater number of frequency bins relative to the number of stimulation channels (electrode channels) simply gives the neural network the ability to apply frequencies to different electrode channels beyond that which would be the case if there were only 22 frequency bins or fewer.

Moreover, it is noted that the way that the neural network applies frequencies to electrode channels is not always the same, and in fact, is frequently dynamically different with respect to a temporal period that is relatively short. In an exemplary embodiment, over a period of seconds, minutes and/or hours, for example, the neural network may apply the same frequency encountered at different temporal periods to two or three or four or more different electrode channels respectively. The neural network may apply frequencies located in different frequency bins to the exact same electrode channel during the temporal periods at issue. In an exemplary embodiment, over a period of seconds, minutes and/or hours, for example, the neural network may apply frequencies that fall within the same frequency bins encountered at different temporal periods to two or three or more different electrode channels respectively. Again, in some embodiments, this can have utilitarian value with respect to enabling the recipient to perceive differences that might not otherwise be perceived, or otherwise perceive differences better than that which would otherwise be the case, all other things being equal.

In an exemplary embodiment, over a period of 0.1, 0.2, 0.3, 0.4, 0.5, 0.6, 0.7, 0.8, 0.9, 1.0, 1.25, 1.5, 1.75. 2, 2.25, 2.5, 2.75, 3, 3.5, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 seconds and/or minutes and/or hours, the neural network will apply frequencies falling within a given frequency bin to at least 2, 3, 4, 5, 6, 7, 8, 9, or 10 different electrode channels (and, in other embodiments, over at least any value or range of values in integer increments of the values of "M" detailed above (e.g., 5 to 100,000, 5 to 250,000, etc.) over respective encounters of such frequencies falling within such frequency bins during the aforementioned time. In an exemplary embodiment, a given distribution might be at least or no more than X % of frequencies of a given frequency bin are applied to a given electrode channel for the aforementioned temporal periods, where X equals 1, 2 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 or any value or range of values therebetween in 0.1% increments.

It is noted that in an exemplary embodiment, the above scenario is executed without changing any settings whatsoever and/or without reprogramming or otherwise changing the program on the hearing prosthesis during the aforementioned temporal periods.

In view of the above, an exemplary method 800 can be represented by the algorithm according to FIG. 8. Method 700 includes method action 810, which includes executing method 300 as detailed above. Again, in this exemplary embodiment, the data contains audio content, and the evoked sensory percept is a hearing percept, although this embodiment can be revised for utilization in a sight prosthesis, etc. Method 800 further includes method action 820, which includes dividing the audio content into N number of frequency bins. Method 800 further includes method action 830, which includes analyzing the content of the frequency bins using the product from the machine learning of method 300, and, based on the analysis, applying the processed content of the frequency bins to M number of electrode channels, wherein M is less than N and at least one of the electrode channels is paired with two or more of the frequency bins, which was different than that which was the case previously based solely due to an analysis by the product of the machine learning. Accordingly, in an exemplary embodiment, if frequency bin number 30 and bin number 33 are utilized for electrode channel 7, at least one of frequency number 30 or frequency number 33 would have been utilized for a electrode channel different than electrode channel 7.

The above exemplary embodiment also raises the issue of the fact that in some embodiments, the application of frequency bins may not necessarily be monotonic and/or not necessarily linear. By way of example only and not by way of limitation, for linear frequency bins, where each bin encompasses frequencies that are larger than that of the prior bin, in some embodiments, frequency bins having higher frequencies will not be applied to electrode channels for lower frequencies, at least when an application for those frequencies is present, and vice versa, while in other embodiments, this is not the case. Thus, by way of example only and not by way of limitation, if frequency bin 20 encompasses 700 Hz, and frequency bin 11 encompasses 750 Hz, and frequency bin 12 encompasses 770 Hz, frequency bin 11 will not be applied to an electrode having a tonotopical mapping that is higher than the electrode for which bin 12 was applied for a given stimulation or otherwise for any of the above noted temporal periods. Conversely, further by way of example only and not by way of limitation, if frequency bin 20 encompasses 700 Hz, and frequency bin 11 encompasses 750 Hz, and frequency bin 12 encompasses 770 Hz, frequency bin 11 can be applied to an electrode having a tonotopical mapping that is higher than the electrode for which bin 12 was applied for a given stimulation or otherwise for any of the above noted temporal periods.

Any order and any application of frequency bins to a given electrode channel that can have utilitarian value can be utilized in at least some exemplary embodiments.

Again, as noted above, the teachings detailed herein can have utilitarian value with respect to enabling a recipient to better distinguish between voices of different people, or at least between male and female voices. Thus, in an exemplary embodiment, frequencies associated with a female voice might be applied to a different electrode channel than that which would be the case for a same frequency of a male voice, providing that such will enhance or otherwise enable the recipient to distinguish between male and female voice.

Also, irrespective of the same frequencies or different frequencies associated with portions of the voice of a woman and/or the voice of a man, where the frequencies will be different, the processing can be different beyond that associated with simply applying the same frequency bands to different electrode channels. In this regard, in an exemplary embodiment of method 300, where the data contains audio content containing the voice of a woman and the voice of a man temporally separated from the voice of the woman, and the evoked sensory percept is a hearing percept, the product from the machine learning processes or otherwise analyzes the content containing the woman's voice and the content containing the man's voice so that respective different electrode channels of a cochlear implant implanted in a person are used to stimulate the cochlea to evoke respective hearing percepts based on the respective contents, the different electrode channels being beyond that which results simply because the frequencies of the contents are different.

Indeed, in an exemplary embodiment, the teachings detailed herein can purposely skew the sound of a person's voice as perceived by the recipient. By way of example only and not by way of limitation, the product based on the machine learning can function so that male voices sound more like James Earl Jones, and female voices sound like Fran Drescher. Moreover, the product can function such that different people sound differently in a manner that is repeatable so that the recipient can better recognize a given voice. By way of example only and not by way of limitation, the product could assign voice types to different people that the recipient encounters based on the person's voice spectrum. For example, voice assignments can correspond to different actors for men and women, or singers for men and women, or well-known people, etc. Alternatively, voice assignments can correspond to people who are unknown but have distinctive voices in any event. Indeed, the voices need not necessarily correspond to any given human being that is alive or otherwise existed, providing that they have a distinctness that is more recognizable than that which would otherwise be the case.

Moreover, in at least some exemplary embodiments, the prosthesis can operate in different modes so that the evoked percept is different for the same given input. First, it is noted that in at least some exemplary embodiments, the activities of the DNN can be controlled or otherwise selectively enabled and/or disabled. By way of example only and not by way of limitation, in some embodiments, the prosthesis can operate as a normal traditional hearing prosthesis even while using the DNN, and in other embodiments, the DNN can be selectively enabled or disabled, where the disabled DNN results in the normal sound processor operating in a normal manner (frequency bins can be funneled into the 22 electrode channels or however many electrode channels so that the normal frequency mapping is what is utilized). Conversely, the prosthesis can be controlled to enable the DNN to do its thing. Moreover, in some embodiments, the DNN can be selectively controlled to operate differently. By way of example only and not by way of limitation, the DNN could operate in a manner such that the sound of one's spouse's voice is perceived as being more sultry or the like, in the hour or two before bedtime, for utilitarian purposes that might otherwise be achieved utilizing certain pills or as a supplement to those pills, and the DNN could transition to another mode that is less exciting or down right non-exciting in the event that a scenario exists where one might otherwise be recommended to seek medical attention because a temporal period extends beyond a certain limit.

The point is, in an exemplary embodiment, the DNN can result in a hearing percept that enhances or otherwise changes certain features of a sound environment beyond that which would result from the normal manipulation of a processing strategy of a hearing prosthesis or a setting of a hearing prostheses or otherwise based on a result associated with an adjustment to the input side processing (beamforming, noise cancellation, etc.) or an adjustment to the output side processing (adjustment of gain of certain electrode channels, deactivation of electrode channels, etc.).

An exemplary embodiment is also represented by the algorithm presented in FIG. 9, which represents method 900. Method 900 includes method action 910, which includes executing method 300, where the data contains audio content, and the evoked sensory percept is a hearing percept. This method also includes method action 920, which comprises, during a first temporal period for a first signal containing audio content of a first type, dividing the audio content into frequency bins. Method 900 also includes method action 930, which includes, again, during that aforementioned first temporal period for the first signal, analyzing the content of the frequency bins using the product that is based on the machine learning and, based on the analysis, applying respective signals based on a first set having respective one or more contents of the frequency bins to respective electrode channels of a cochlear implant implanted in a person.

As seen, method 900 also includes method action 940, which includes, during a second temporal period before and/or after the first temporal period for a second signal containing audio content of a second type, dividing the audio content of the second signal into frequency bins method 900 also includes method action 950, which includes, again during the second temporal period for the second signal, analyzing the content of the frequency bins using the product and, based on the analysis, applying respective signals based on a second set having respective one or more contents of the frequency bins to respective electrode channels of a cochlear implant implanted in a person. In an exemplary embodiment of method 900, the first set is different from the second set, and in other embodiments, the first set is the same as the second set.

Another exemplary embodiment is as follows, which includes a method that entails executing method 300, where the data contains audio content and the evoked sensory percept is a hearing percept. The method further comprises, during a first temporal period for a first signal containing audio content of a first type, dividing the audio content of the first signal into respective frequency bins. Again, by way of example only and not by way of limitation, frequencies falling within a first range can go into frequency bin 33, and frequencies falling within a second range immediately adjacent and higher than the first range can fall into frequency bin 34, and frequencies falling within a third range immediately adjacent and higher than the second range can fall into frequency bin 35. The method further includes during the first temporal period, analyzing the content of the respective frequency bins using the product and, based on the analysis, applying respective signals based on one or more respective contents of the respective frequency bins to respective electrode channels of a cochlear implant implanted in a person. In an exemplary embodiment, a third signal is provided to electrode channel 7, and that third signal is based on the content of frequency bin 34, and a fourth signal is provided to electrode channel 8, and that fourth signal is based on the content of frequency bin 35.

This exemplary method further comprises, during a second temporal period before and/or after the first temporal period for a second signal containing audio content of a second type, dividing the audio content of the second signal into respective frequency bins. In an exemplary embodiment, there is no frequency content in bin 33, but there is content in bins 34 and 35, where the parameters of the frequencies associated there with are? the same. The method further includes analyzing the content of the respective frequency bins using the product. Further, based on the analysis, applying respective signals based on one or more respective contents of the respective frequency bins to respective electrode channels of the cochlear implant implanted in the person.

In this exemplary method, a fifth signal is provided to electrode channel 6, and that fifth signal is based on the content of frequency bin 34. Thus, in this exemplary method, a content of a first frequency bin is applied to one electrode channel during the first temporal period and the content of that first frequency bin is applied to another, different electrode channel, during the second temporal period.

In an alternate embodiment, a fifth signal is provided to electrode channel 7, and that fifth signal is based on the content of frequency bin 34 and 35. Thus, in this exemplary method, a content of a first frequency bin is applied to one electrode channel during the second temporal period and the content of that first frequency bin is applied to another, different electrode channel, during the first temporal period.

In an exemplary embodiment, the frequency bin shifting from one electrode channel to another is repeated 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 times or more in a time span within any of the aforementioned temporal periods. It is briefly noted that one frequency shifting corresponds to the aforementioned scenario where a frequency was applied to two separate electrode channels. If the frequency is applied to that same electrode channel without intervening electrode channel change, that is not a frequency shift, whereas if the frequency is applied to a prior electrode channel that is different than the electrode channel to which was applied in close temporal proximity thereto, that is a frequency shift (or to another electrode channel). Note also that the aforementioned values correspond to the total number of frequency bins in any given stimulation period. For example, in an exemplary embodiment where the electrodes are stimulated sequentially, if electrode channel 7 constitutes a frequency shift, and then electrode channel 9 also constitutes a frequency shift, that is two frequency shifts. Hence the relatively high number of frequency shifts that can exist within a given temporal period.

Again, in at least some exemplary embodiments, these frequency shifts occur solely due to the action of the product that is based on the neural network/DNN. No setting of the prosthesis is changed by a recipient or by an automated system outside of the DNN, at least in some embodiments.

An exemplary embodiment can have utilitarian value with respect to listening to music. As noted above, music can have frequencies that are close to each other that may not be distinguished utilizing a typical cochlear implant sound processing system or any other hearing prosthesis sound processing system some instances. The teachings detailed herein can have utilitarian value with respect to differentiating between instruments in addition to or otherwise distinguishing/differentiating between voices. Indeed, in an exemplary embodiment, instruments of different types can play at the same frequencies. The cochlear implant may not necessarily evoke a hearing percept that differentiates between the two or more instruments playing at the same frequencies or frequencies that are close to one another. With reference to method 300, where the data contains audio content in the form of music, and the output is used to stimulate tissue of a recipient to evoke a hearing percept via a cochlear implant implanted in a person, the product based on the machine learning algorithm or system analyzes the signal to adjust at least one of a perceived timbre, perceived texture or perceived tone, beyond that which results from frequency division and electrode channel mapping.

Note also that in at least some exemplary embodiments, the same frequencies can be applied to different electrode channels so that the recipient can perceive a difference between instruments. Further, such can be applicable to vocals, where two or more people are singing at the same time. The product based on the machine learning can result in a hearing percept where the recipient can differentiate between the two singers.

Other exemplary embodiments can include, such as, for example, where the input subsystem includes a microphone configured to capture sound of an ambient environment, a neural network that is configured to identify a sound environment based on a signal from the microphone that is based on sound captured by the microphone. In an exemplary embodiment, this can correspond to a pseudo-scene classification. Some hearing prostheses have the ability or otherwise have access to scene classification algorithms, which algorithms can, for example, classify a scene as a music environment, a traffic environment, and worksite environment, etc. In an exemplary embodiment, the DNN can detect or otherwise react to a sound environment in a manner analogous to that which would be the case for a scene classifier. Indeed, the DNN does not so much detect as it reacts in a manner that is analogous to reaction based on detection of a sound environment. Again, the functionalities disclosed herein do not necessarily require that the DNN actually have that functionality, only that the DNN be able to operate as if that functionality existed. The nature of artificial intelligence as that phrase is utilized broadly does not require a "conscious" analysis as much as it requires reaction to stimulus that would otherwise be analyzed. It is briefly noted that in some embodiments, the DNN is not necessarily classifying sound or the like. Instead, the DNN is simply operating according to its training, and reacting accordingly. The end result in some embodiments is what would happen if a scene classifier were operating. To be clear, in an exemplary embodiment, there are devices, systems, and/or methods that result in the functionality of scene classification without a scene classifier.

Corollary to the above is that in at least some exemplary embodiments, the DNN enhances sound clarity relative to that which would be the case in the absence of the DNN.

In an exemplary embodiment, the aforementioned differences between the absence of the implementation of the product based on the neural network and/or DNN is a at least a 10, 20, 30, 40, 50, 60, 70, 80, 90, 100, 125, 150, 175, 200, 250, 300, 350, 400, 450, 500, 550, 600, 650, 700, or 750 or more percent increase as measured using any applicable standardized test that can enable such percent determination.

In an exemplary embodiment, the teachings detailed herein can be utilized to improve the ability to distinguish between certain sounds, such as, for example, rain, fan operation, car sounds, sounds of household appliances, etc. Moreover, the teachings detailed herein can be utilized to replicate sounds that are influenced by the medium through which the sounds are conveyed. By way of example only and not by way of limitation, in an exemplary embodiment, the teachings detailed herein can be utilized to replicate the sound of a person speaking on the phone versus the sound of that same person in the same room with the recipient.

In view of the above, it can be seen that in an exemplary embodiment, there is a device, comprising a hearing prosthesis including an input subsystem configured to receive input based on sound and a sound processor configured to process data based on input into the input subsystem. In this exemplary embodiment, the hearing prosthesis includes a product of and/or from machine learning that is used by the hearing prosthesis to evoke a hearing percept based on input into the input subsystem. Consistent with the teachings detailed above, in an exemplary embodiment, the hearing prosthesis is a cochlear implant, and the product results in stimulation of a recipient of the hearing prosthesis on a first electrode channel during a first temporal period for a given frequency and on a second electrode channel for that same frequency during a second temporal period. In an exemplary embodiment, this results without any adjustment or any change in settings or without any reprogramming of the hearing prosthesis. To be clear, in an exemplary embodiment, at a minimum, the same map settings are utilized when this occurs. In an exemplary embodiment, the aforementioned first and second temporal periods occur within any of the temporal periods detailed herein. In this exemplary embodiment, this can be executed within a matter of a second or two, for example. Consistent with the teachings detailed above, the product adjusts a frequency domain of the data based on the input on a variable basis before reaching a map section of the hearing prosthesis.

In an exemplary embodiment, the hearing prosthesis is configured so as to obtain at least an equivalent number of input side processing filter banks that is substantially more than the number of stimulation electrode channels of the hearing prosthesis.

In an exemplary embodiment, again where the hearing prosthesis is a cochlear implant, the product of/from the machine learning is code or chip or circuitry or any arrangement that adjusts, in real time, at least one of an amplitude, pulse width, rate of stimulation, interphase gap or maxima location of output of the cochlear implant. In an exemplary embodiment, adjusting these and/or any other feature that is adjusted as detailed herein can be utilitarian with respect to achieving or otherwise improving the likelihood that the recipient will be able to, and effectively be able to, extract or otherwise recognize useful sound in a noisy environment, experience an expanded dynamic range with respect to certain types of sounds, be able to better differentiate voices/instruments/sources of sound, and hear or otherwise experience and enhance sound clarity, all relative to that which would otherwise be the case with respect to utilizing something other than a neural network associated processor, such as, any of the sound processing strategies detailed herein or variations thereof or otherwise known that are different than the teachings detailed herein.

In an exemplary embodiment, the prostheses detailed herein are configured such that the code extracts useful sound in a noisy environment beyond that which would be the case in the absence of the product, all other things being equal.

Some embodiments include teaching the neural network to perform its sound processing task. In some embodiments, the neural network is a fully taught neural network. In some embodiments, it is a partially taught neural network that is trainable with use of the hearing prosthesis. In some embodiments, it is a fully taught neural network that can be updated.

One learning process is performed to give the network the ability to process a multitude of sounds into preferred electrical stimulus. Embodiments include executing this, online or offline by, for example, determining the "ideal" desired stimulation for a given audio signal, and then teaching the neural network to produce such stimulus from the various sounds it is presented with. In some embodiments, the ideal desired stimulation can be derived by any number of methods including complex filter mechanisms, etc., which can take significant offline processing power. This heavy processing to derive the ideal desired stimulation can be managed via execution offline. In some embodiments, this is done only once, and no more. When the network has been adequately taught to produce these ideal stimuli from the various different sound sources, the network configuration is then loaded into the implant neural network and it will perform as intended in the field.

The above said, in some embodiments, there is continued improvement in the neural network performance offline, and the network is periodically updated, and the implant neural network is periodically updated with improved configurations, allowing for post implantation improvements ("upgrades") to the system.

Another way of doing this, which can be optional, is to execute an optional learning process that can improve the performance of the neural network on an individual-recipient basis, by teaching the neural network to improve its operation based on feedback from the recipient during operation in the field. A mechanism can be implemented that allows the recipient to signal to the implant neural network if the electrical audio stimulation being received for whatever sound environment that is currently present is giving good results or not so good results or otherwise is a candidate for change (or not). This feedback can be then used to reconfigure the neural network configuration (node weights) based on a reward function to try to improve the outcome. If this mechanism is used, periodic updates of the neural network from offline processing improvements (as described in the first learning process) become difficult as these would reset any recipient specific improvements/changes that have been made.

Some embodiments can utilize any form of the genus known as artificial intelligence. The teachings above are generally focused on neural networks. In at least some exemplary embodiments, a deep neural network, such as a back propagated deep neural network, is utilized. It is noted that in some other embodiments, other types of artificial intelligence are utilized, such as by way of example only and not by way of limitation, expert systems. That said, in some embodiments, the neural network is specifically not an expert system, consistent with the fact that any disclosure of any embodiment herein constitutes a corresponding disclosure of an embodiment that specifically does not have that embodiment.

Embodiments include the utilization of a system that does not have a set of hard parameters from which decisions are derived. Embodiments can include parameters that cover the entire spectrum of possible inputs. In some embodiments, the neural networks detailed herein do not operate on specific parameters, but rather creates its own internal weight structures (in the learning process) that more loosely operate on a multitude of subtle characteristics of the input rather than a set of hard externally defined parameters. This can have utilitarian value with respect to allowing the neural network to focus on the significant aspects of the input and ignore those parts that do not contribute much useful information.

In at least some exemplary embodiments, there exists the application of evoking hearing percepts for certain frequencies that are captured at different threshold and/or comfort levels than that which would otherwise be the case for normal application. In this regard, as noted above, in some exemplary embodiments, the content of frequency bins is moved from one electrode channel to another. In this regard, for a given electrode channel, there is a specific threshold and/or comfort level as compared to another electrode channel. Accordingly, the teachings detailed herein can result in a captured frequency having a specific signal amplitude being utilized to evoke a hearing percept at a first energy level and then upon the reoccurrence of that frequency at that same amplitude, there exists the evoking of a hearing percept at a second energy level which is different than the first energy level, without any adjustments to a volume or the like or a gain or the like of the prostheses, which can occur within any of the temporal periods detailed herein, and of course, in some embodiments, there can be the reoccurrence of that where the first energy level is again used, and/or there can be a third energy level that exist for that same frequency at that same amplitude, which is different than the first and the second, and so on. It is also noted that in at least some exemplary embodiments, the scaling is different with respect to the amplitude of the captured signal. For example, in a scenario where the given frequency is recaptured, but the magnitude of the signal for that frequency is different, the scaling that occurs with respect to the transposition from the signal strength in the ambient environment to the energy that is applied to the cochlea can be different for a given electrode channels, again, based on the fact that the different electrode channels have different comfort and/or threshold levels.

Any learning model that is available and can enable the teachings detailed herein can be utilized in at least some exemplary embodiments. As noted above, an exemplary model that can be utilized with voice analysis and other audio tasks is the Deep Neural Network (DNN). Again, other types of learning models can be utilized, but the following teachings will be focused on a DNN.

According to an exemplary embodiment of developing a learning model, a learning model type is selected and structured, and the features and other inputs are decided upon and then the system is trained. It needs to be trained. In exemplary embodiments of training the system, a utilitarian amount of real data is compiled and provided to the system. In an exemplary embodiment, the real data comprises any data having utilitarian value. The learning system then changes its internal workings and calculations to make its own estimation closer to, for example, the actual person's hearing outcome. This internal updating of the model during the training phase can improve (and should improve) the system's ability to correctly control the prosthesis. Subsequent individual subject's inputs and outputs are presented to the system to further refine the model. With training according to such a regime, the model's accuracy is improved. In at least some exemplary embodiments, the larger and broader the training set, the more accurate the model becomes.

In the case of a DNN, the size of the training can depend on the number of neurons in the input layer, hidden layer(s), and output layer.

There are many packages now available to perform the process of training the model. Simplistically, the input measures are provided to the model. Then the outcome is estimated. This is compared to the subject's actual outcome, and an error value is calculated. Then the reverse process is performed using the actual subject's outcome and their scaled estimation error to propagate backwards through the model and adjust the weights between neurons, and improving its accuracy (hopefully). Then a new subject's data is applied to the updated mode, providing a (hopefully) improved estimate. This is simplistic, as there are a number of parameters apart from the weight between neurons which can be changed, but generally shows the typical error estimation and weight changing methods for tuning models according to an exemplary embodiment.

Figure 10:
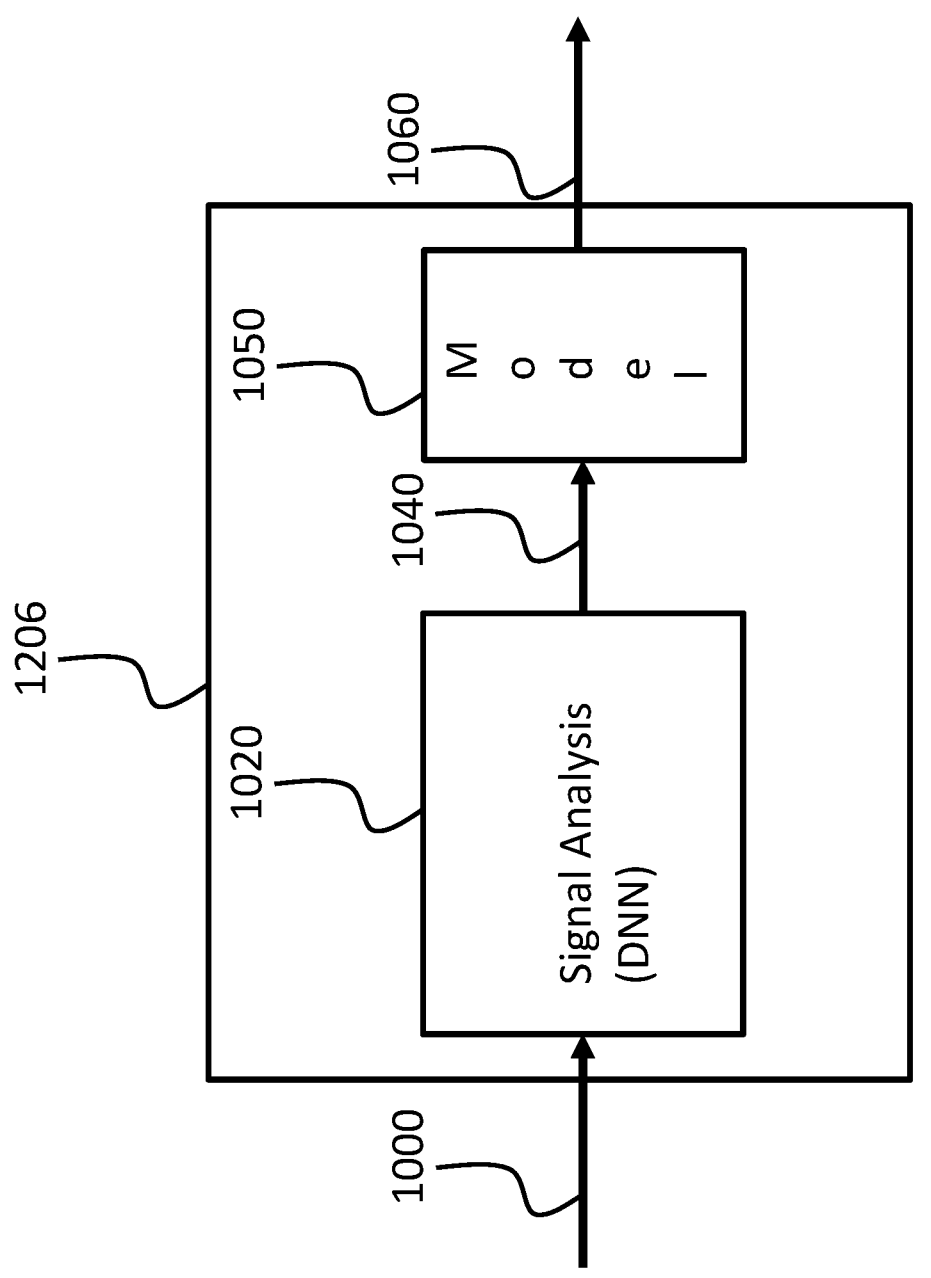
FIG. 10 presents an exemplary functional diagram for an exemplary embodiment.

A system utilized to train a DNN or any other machine learning algorithm or system, along with acts associated therewith, is now described. The system will be described, at least in part, in terms of interaction with a recipient, although that term is used as a proxy for any pertinent subject to which the system is applicable (e.g., the test subjects used to train the DNN, the subject utilized to validate the trained DNN.). In an exemplary embodiment, system 1206, as seen in FIG. 10, is a recipient-controlled system while in other embodiments, it is a remote-controlled system. In an exemplary embodiment, system 1206 can correspond to a remote device and/or system, which, as detailed above, can be a portable handheld device (e.g., a smart device, such as a smart phone), and/or can be a personal computer, etc. In an exemplary embodiment, the system is under the control of an audiologist or the like, and subjects visit an audiologist center.

Figure 11:
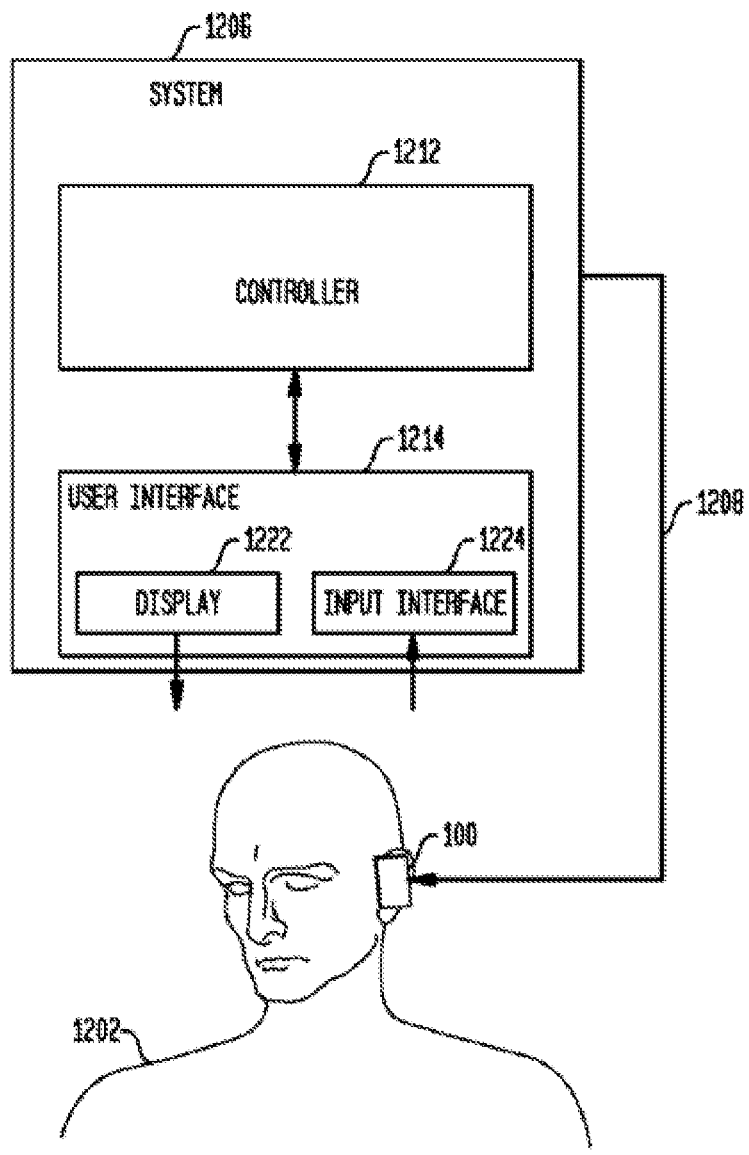
FIG. 11 presents another exemplary functional diagram for an exemplary embodiment.

In an exemplary embodiment, the system can be a system having additional functionality according to the method actions detailed herein. In the embodiment illustrated in FIG. 11, the device 100 can be connected to system 1206 to establish a data communication link 1208 between the hearing prosthesis 100 (where hearing prosthesis 100 is a proxy for any device that can enable the teachings detailed herein, such as a smartphone with a microphone, a dedicated microphone, a phone, etc.) and system 1206. System 1206 is thereafter bi-directionally coupled by a data communication link 1208 with hearing prosthesis 100. Any communications link that will enable the teachings detailed herein that will communicably couple the implant and system can be utilized in at least some embodiments.

System 1206 can comprise a system controller 1212 as well as a user interface 1214. Controller 1212 can be any type of device capable of executing instructions such as, for example, a general or special purpose computer, a handheld computer (e.g., personal digital assistant (PDA)), digital electronic circuitry, integrated circuitry, specially designed ASICs (application specific integrated circuits), firmware, software, and/or combinations thereof. As will be detailed below, in an exemplary embodiment, controller 1212 is a processor. Controller 1212 can further comprise an interface for establishing the data communications link 1208 with the hearing prosthesis 100 (again, which is a proxy for any device that can enable the methods herein-any device with a microphone and/or with an input suite that permits the input data for the methods herein to be captured). In embodiments in which controller 1212 comprises a computer, this interface may be, for example, internal or external to the computer. For example, in an exemplary embodiment, controller 1206 and cochlear implant may each comprise a USB, FireWire, Bluetooth, Wi-Fi, or other communications interface through which data communications link 1208 may be established. Controller 1212 can further comprise a storage device for use in storing information. This storage device can be, for example, volatile or non-volatile storage, such as, for example, random access memory, solid state storage, magnetic storage, holographic storage, etc.

In an exemplary embodiment, input 1000 is provided into system 1206. The DNN signal analysis device 1020 analyzes the input 1000, and provides output 1040 to model section 1050, which establishes the model that will be utilized for the trained device. The output 1060 is thus the trained neural network, which is then uploaded onto the prostheses or other component that is utilized to implement the trained neural network.

Here, the neural network can be "fed" statistically significant amounts of data corresponding to the input of a system and the output of the system (linked to the input), and trained, such that the system can be used with only input, to develop output (after the system is trained). This neural network used to accomplish this later task is a "trained neural network." That said, in an alternate embodiment, the trained neural network can be utilized to provide (or extract therefrom) an algorithm or system that can be utilized separately from the trainable neural network. In one exemplary embodiment, a machine learning algorithm or a machine learning system starts off untrained, and then the machine learning algorithm or system is trained and "graduates" or matures into a usable product—the product of a trained machine learning system. With respect to another exemplary embodiment, the product from the trained machine learning—is the "offspring" of the trained machine learning (or some variant thereof, or predecessor thereof), which could be considered a mutant offspring or a clone thereof. That is, with respect to this second path, in at least some exemplary embodiments, the features of the machine learning system that enabled the machine learning system to learn may not be utilized in the practice of the first path, thus are not present in the first version. Instead, only the resulting product of the learning is used.

In an exemplary embodiment, the product from and/or of the machine learning utilizes non-heuristic processing to develop the data utilized in the trained system. In this regard, the system takes sound data or takes in general relating to sound, and extracts fundamental signal(s) there from, and uses this to develop the model. By way of example only and not by way of limitation, the system utilizes algorithms beyond a first-order linear algorithm, and "looks" at more than a single extracted feature. Instead, the algorithm "looks" to a plurality of features. Moreover, the algorithm utilizes a higher order nonlinear statistical model, which self learns what feature(s) in the input is important to investigate. As noted above, in an exemplary embodiment, a DNN is utilized to achieve such. Indeed, in an exemplary embodiment, as a basis for implementing the teachings detailed herein, there is an underlying assumption that the features of the sound and other input into the system that enable the model to be generated may be too complex to be specified, and the DNN is utilized in a manner without knowledge as to what exactly on which the algorithm is basing its determinations/at which the algorithm is looking to develop the model.

In at least some exemplary embodiments, the DNN is the resulting product used to make the prediction. In the training phase there are many training operations algorithms which are used, which are removed once the DNN is trained.

To be clear, in at least some exemplary embodiments, the trained algorithm or system is such that one cannot analyze the trained algorithm or system with the resulting product therefrom to identify what signal features or otherwise what input features are utilized to produce the output of the trained neural network. In this regard, in the development of the system, the training of the algorithm or system, the system is allowed to find what is most important on its own based on statistically significant data provided thereto. In some embodiments, it is never known what the system has identified as important at the time that the system's training is complete. The system is permitted to work itself out to train itself and otherwise learn to control the prosthesis.

Briefly, it is noted that at least some of the neural networks or other machine learning systems utilized herein do not utilize correlation, or, in some embodiments, do not utilize simple correlation, but instead develop relationships. In this regard, the learning model is based on utilizing underlying relationships which may not be apparent or otherwise even identifiable in the greater scheme of things. In an exemplary embodiment, MatLAB, Buildo, etc., are utilized to develop the neural network. In at least some of the exemplary embodiments detailed herein, the resulting train system is one that is not focused on a specific speech feature, but instead is based on overall relationships present in the underlying statistically significant samples provided to the system during the learning process. The system itself works out the relationships, and there is no known correlation based on the features associated with the relationships worked out by the system.

The end result is a product which is agnostic to sound features. That is, the product of the trained neural network and/or the product from the trained neural network is such that one cannot identify what sound features are utilized by the product to develop the production (the output of the system). The resulting arrangement is a complex arrangement of an unknown number of features of sound that are utilized. In embodiments utilizing code, the code is written in the language of a neural network, and would be understood by one of ordinary skill in the art to be such, as differentiated from a code that utilized specific and known features. That is, in an exemplary embodiment, the code looks like a neural network. This is also the case with the products detailed herein. The product looks like a neural network, and the person of skill would recognize such and be able to differentiate that from something that has other origins.

Consistent with common neural networks, there are hidden layers, and the features of the hidden layer are utilized in the process to predict the hearing impediments of the subject.

The product or the DNN, etc., can control various aspects of the output of the prosthesis. Indeed, output side functionalities can have various sub-functions that can be implemented and/or not implemented and/or otherwise varied under the control of the DNN. In this regard, FIG. 12 depicts an exemplary functional schematic of an operation of at least a portion of the output side stages as a conceptual amalgamation where input from the input side enters the output side processing, which includes various blocks as will now be detailed, which results in output 390 that is utilized to evoke a sensory percept, such as a hearing percept in this exemplary embodiment.

It is noted that in some instances, the following blocks will be described in terms of the blocks controlling a given feature. This is for purposes of linguistic economy. It is noted that in some instances, these are features that cannot necessarily be identified within the DNN. Indeed, as with all aspects of the DNN, there is more of a functionality associated there with as opposed to a specific section does a certain thing. In this regard, while the following is often described in terms of a block or a sub component or a subsystem of the prosthesis, such also corresponds to the disclosure of a product or a DNN, etc., that when operating, has this functionality owing to its training.

In an exemplary embodiment, the DNN or the code, or the product, etc., can be utilized to vary any of the features associated with any of the following blocks. In an exemplary embodiment, the output side processing 1200 includes a timing block 1210. Timing block 1210 is utilized to determine the stimulation rate(s) that will be applied to the tissue stimulator, at least with respect to electrical stimulation. By way of example only and not by way of limitation, an electrode of a retinal implant may be stimulated at a rate of 1000 pulses per second, whereas in at least some exemplary embodiments, there may be utilitarian value to instead stimulate at a rate of 500 pulses per second. Still further by way of example, with respect to a cochlear implant, an exemplary stimulation rate of given electrode that is being utilized to evoke a hearing percept is at about 900 pulses per second, whereas in some alternate embodiments, there can be utilitarian value with respect to stimulating at a rate of 500 pulses per second, a slower rate. In an exemplary embodiment, stimulation can occur for a given electrode from about 5000, 4750, 4500, 4250, 4000, 3750, 3500, 3250, 3000, 2750, 2500, 2250, 2000, 1900, 1800, 1700, 1600, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, 200, 150, 100, or 50 or any value or range of values therebetween in 1 pulse per second increments. To be clear, these data points/ranges are but exemplary (as is the case with respect to all of the data points detailed herein unless otherwise specified). In some embodiments, stimulation can occur for a given electrode at ranges above these values or below these values. As will be disclosed herein, an exemplary embodiment entails operating a sense prosthesis during a first temporal period where the stimulation rate occurs at about 900 pulses per second, and then, due to a scenario that will be described in greater detail below, operating the hearing prosthesis such that the stimulation rate occurs at about 500 pulses per second. Still further, in an exemplary embodiment, there can be a scenario where the hearing prosthesis is operated such that the stimulation rate that occurs is about 700 pulses per second.

Figure 12:
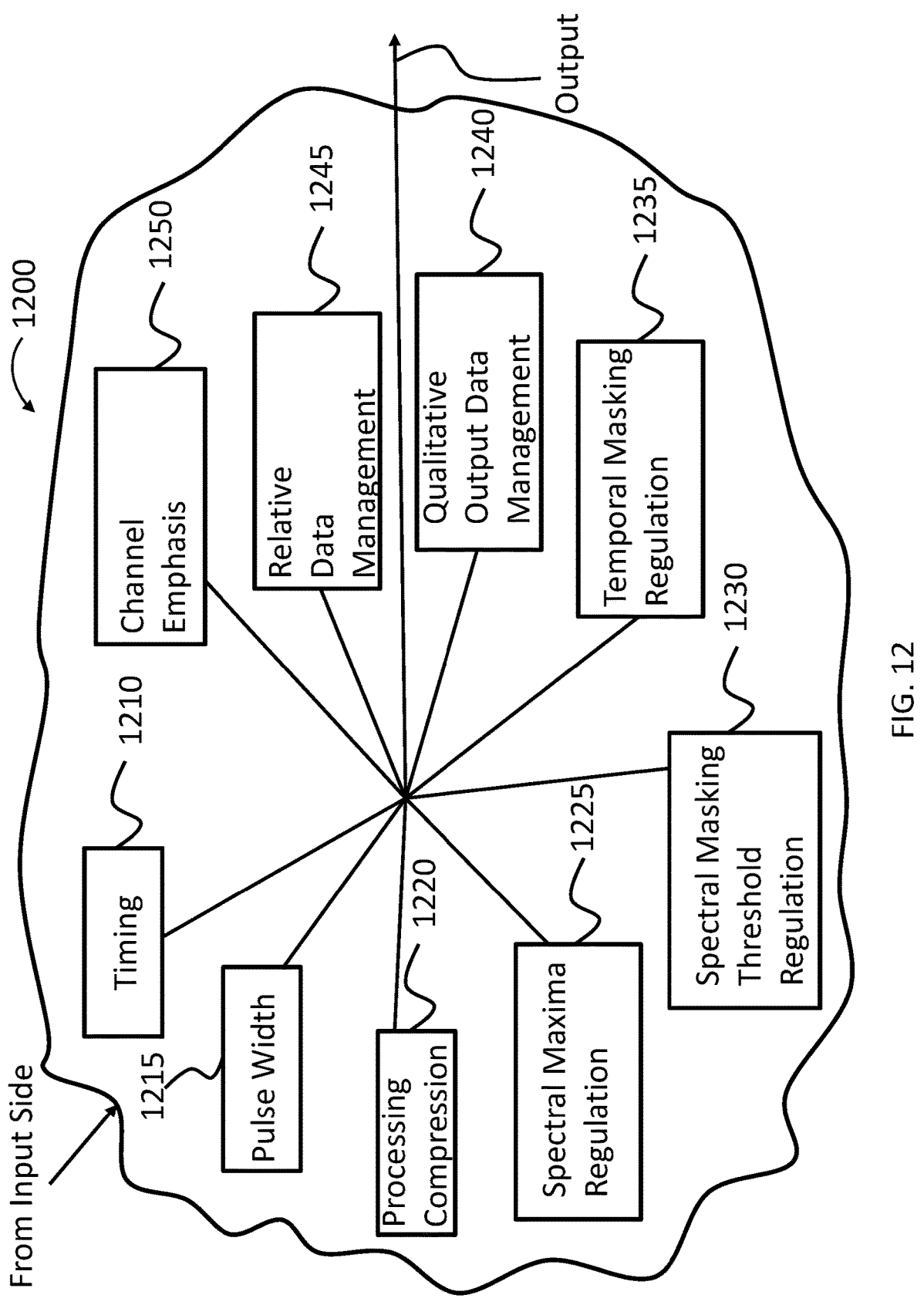
FIG. 12 presents another exemplary functional diagram for an exemplary embodiment.

Still with reference to FIG. 12, output side processing 1200 includes a pulse width block 1215. Pulse width block 1215 determines the pulse widths of the stimulation signals applied to the electrodes. In an exemplary embodiment, the pulse width can be from about 75 μs, 70 μs, 65 μs, 60 μs, 55 μs, 50 μs, 45 μs, 40 μs, 35 μs, 30 μs, 25 μs, 20 μs, 15 μs, 10 μs, 5 μs, or any value or range of value therebetween in 1 μs increments. As with the timing block 310, the hearing prosthesis can be operated depending on a range of scenarios to have different pulse widths as will be detailed herein by way of example only and not by way of limitation.

Still further, output side processing 1200 includes compression block 1220. In an exemplary embodiment, the prosthesis utilizes a signal processing strategy that is consistent for some instances, such as, as noted above, a standard sound processing regime. That is, this can be considered to be a default speech processing strategy. With respect to a hearing prosthesis, such can be the ACE processing strategy, or some other processing strategy that does not utilize perceptual coding concepts. That said, in some exemplary scenarios, there can be utilitarian value with respect to utilizing a different processing strategy or otherwise implementing a modification of the given processing strategy. In an exemplary embodiment, such entails utilizing a processing strategy that utilizes psychophysical processing strategies that utilize perceptual coding concepts that can, for example, take into account the fact that some environmental inputs (sound, light, etc.) are perceptually masked by other inputs (sound, light—this is sometimes referred to in the art as a masking phenomenon), and therefore need not be presented as stimulation components (audio, visual component, depending on the embodiment). Masking functionally can result in fewer spectral components (or maxima) that are ultimately coded. In at least some exemplary embodiments of the embodiments detailed herein, the prosthesis changes from a non-psychophysical processing strategy to a psychophysical processing strategy upon the occurrence of a different scenario, again which will be detailed below. In an exemplary embodiment with respect to a hearing prosthesis, the psychophysical sound processing strategies used in at least some of these exemplary embodiments utilize masking models to estimate effects of the masking phenomena on a recipient, and in turn, to process and encode received sound information into corresponding encoded electronic signals that may omit sounds that would be perceptually masked. A similar concept can be utilized with respect to light for a retinal prosthesis.

Accordingly, in an exemplary embodiment, there is a psychophysical processing strategy, such as a sound processing strategy, can depend in part on sound intensity parameters.

It is noted that some prior art prostheses utilize the ACE or modified ACE sound processing strategy, known in the art as the ACE with MP3 superscript 000 considerations, such as that detailed in U.S. Pat. No. 7,272,446 to John Parker, who at the time that the application was filed (Aug. 21, 2001, by way of the PCT, and Aug. 21, 2000, by way of the priority Australian patent application PQ 9528), performed his innovative work in Lane Cove, NSW, Australia, Mr. Parker being a citizen of Australia. Other sound processing strategies exist as well.

Exemplary embodiments include processing sound explicitly without utilizing such sound processing strategies. Indeed, instead of a sound processing strategy, there are the results of a trained neural network.

Some of the DNNs manage spectral maxima, and can do so in a manner that does not have a fixed quantitative value, but can achieve spectral masking based on the size of the given maxima. In this regard there can be a spectral masking threshold regulation block. In this vein, output side processing 1200 includes spectral masking threshold regulation block 1230. The spectral masking threshold regulation block adjusts a slope of the masking (the masking slope) to impact frequencies that are at either higher or lower frequencies than an input at issue. Accordingly, in an exemplary embodiment, the spectral masking threshold regulation block 330 regulates the masking slope that will be utilized with respect to the output side. In some exemplary embodiments, the prosthesis will be utilized in some scenarios to have a slope that is less steep, more gradual than that which was the case in other scenarios, thus eliminating spectral maximas that otherwise might be present with a steeper slope.

Still further, with continuing reference to FIG. 12, as can be seen, output side processing 1200 further includes a temporal masking regulation block 1235. In this regard, in an exemplary embodiment, the prosthesis can vary the temporal masking offsets that are utilized during exemplary scenarios (which includes implementing embodiments where there is no temporal offset—it is noted that all of the examples herein include utilizing the prostheses without the implementation of a functionality of a given block—for example, there can be no processing compression, no spectral maxima regulation, no spectral masking threshold regulation, etc., in some scenarios).

More specifically, masking can also have a temporally forward and/or backward impact. Forward masking occurs when the sound following a masker cannot be heard, and backward masking occurs when a masker follows the sound. With respect to a hearing prosthesis, a forward masker generally impacts sound thresholds approximately 100-200 ms following the masker, and a backward masker generally impacts sound thresholds approximately 10 ms prior to the masker. Similar concepts are applicable for a vision prosthesis, such as a retinal implant. In this regard, a forward masking offset of 200-250 ms is greater than a forward masking offset of 100-200 ms, and thus will eliminate more following input than the latter, and a backward masking offset of 150 ms is greater than a backward masking offset of 100 ms, and thus will eliminate more prior input than the latter. Both latter offsets will result in less data being provided to the recipient of the output of the prosthesis than that which would be the case with respect to the respective former offsets.

Again, continuing with reference to FIG. 12, output side processing 1200 further includes spectral maxima regulation block 125. While the processing compression block 1220 does result in fewer maxima due to the reduction in processing, embodiments, also can artificially limit the number of maxima of the given processing compression strategy resulting from block 1220, relative to that which would be the case in the absence of maxima regulation. In an exemplary embodiment, fewer maxima results in less stimulation relative to that which would be the case with more maxima, all other things being equal.

As noted above, some exemplary embodiments utilize noise cancellation techniques in the input side of the processing. Conversely, embodiments can also utilize and/or instead utilize noise mitigation techniques on the output side. With continued reference to FIG. 12, it can be seen that the output side processing 1200 further includes qualitative output data management block 120. In this regard, block 1240 implements or otherwise provides stimulus mitigation/stimulus reduction in the form of stimulus reduction algorithms. In an exemplary embodiment, these stimulus reduction algorithms can reduce the amount of stimulus based on light that is captured that is provided to the recipient. In this regard, embodiments include light mitigation/light reduction algorithms. With respect to hearing prosthesis, some exemplary embodiments include sound mitigation algorithms and sound reduction algorithms. It is noted that in general, the processing strategies in at least some exemplary embodiments that are directed to a hearing prosthesis, irrespective of the presence of block 1240, employ a brightening (highpass) filter to suppress low-frequency audio information. That said, in some exemplary embodiments, block 1240 can implement adaptive dynamic range optimization to focus processing on sound intensities that have a higher probability of being associated with sound that is deemed to be desired. With respect to vision prostheses, the processing strategy can also include a brightening strategy and/or a darkening strategy, with similar conceptual results. That said, in some exemplary embodiments, block 1240 can implement adaptive dynamic range optimization to focus processing on light intensities that have a higher probability of being associated with light that is deemed to be desired.

Thus, in an exemplary embodiment, such as an embodiment where the ambient environment is bright (in the light sense) and/or noisy (in the sound sense), block 1240 is utilized to focus processing on light and/or sound intensities that have a higher probability of being associated with moving objects, for example, and with speech, respectively, for example, depending on the type of prosthesis in which the teachings detailed herein are implemented.

It is noted that block 1240 is differentiated from the other types of light and noise reduction that can achieve by single cancellation, or the other types of light and noise management that can be achieved by, for example, beamforming, both of which are associated with input side of the processing.

In the embodiment represented by FIG. 12, in some exemplary embodiments, the output side processing 1200 further includes a relative data management block 1245. In an exemplary embodiment, relative data management block 1245 manages the output of the hearing prosthesis, or more accurately, processes on the output side the output of the hearing prosthesis such that the output is relativized. By way of example only and not by way of limitation, embodiments can utilize light growth and loudness growth functions. With respect to loudness growth (identified as the Q factor in the art), loudness growth defines how the acoustic dynamic range is mapped into electric output. This corresponds to the role acoustic dynamic range that the processing can optimize. However, in at least some exemplary embodiments, when Q values increase, more information is mapped onto the audible levels. This can entail increasing the amount of "noisy" information that is mapped onto the audible levels. In at least some exemplary embodiments, this can have a deleterious effect in that the noisy information can crowd out the information that is wanted or otherwise desirable, or can crowd out information that is more wanted or otherwise more desirable relative to the additional information that is inputted into the audible spectrum. A similar concept applies to vision prostheses where an increase in brightness can crowd out information that is more desirable and more useful to the recipient relative to the additional information that is inputted due to the increase in brightness.

Still further with respect to FIG. 12, the output side processing 1200 further includes channel emphasis block 1250. As noted above, in some exemplary embodiments of the prostheses detailed herein and/or variations thereof, the input is divided up into channels, such as by way of example, by the filter block. Channel emphasis block 1250 can emphasize some of these channels over others. Indeed, in an exemplary embodiment, channel emphasis block 1250 emphasizes some channels by eliminating other channels, or more specifically, eliminating the output of one or more given channels from the output of the output side processing 1200. Still further, in an exemplary embodiment, channel emphasis block 1250 can emphasize some channel(s) by reducing the magnitude/amplitude of the output signal of some channel(s) relative to others, instead of eliminating those channel(s) entirely. Corollary to this is in that in at least some exemplary embodiments, channel emphasis block 1250 can emphasize some channels by increasing the magnitude/amplitude of the output signal of some channel(s) relative to others, all other things being equal.

In an exemplary embodiment, there can be scenarios where the information on one or more given channels is deemed more useful to a recipient then information on one or more other channels. However, the information on the one or more other channels makes it more difficult to understand the information on the one or more channels where the information is deemed more useful, at least relative to the scenario where if the information in those other channels that is deemed not as useful were not present. Accordingly, in an exemplary scenario, channel emphasis block 1250 can be utilized to operate the hearing prosthesis such that one or more channels are emphasized over one or more other channels (which includes deemphasizing, including eliminating, channels) with respect to the output of the output side processing 1200.

It is noted that any method detailed herein also corresponds to a disclosure of a device and/or system configured to execute one or more or all of the method actions associated there with detailed herein. In an exemplary embodiment, this device and/or system is configured to execute one or more or all of the method actions in an automated fashion. That said, in an alternate embodiment, the device and/or system is configured to execute one or more or all of the method actions after being prompted by a human being. It is further noted that any disclosure of a device and/or system detailed herein corresponds to a method of making and/or using that the device and/or system, including a method of using that device according to the functionality.

Any action disclosed herein that is executed by the prosthesis 100 can be executed by the device 240 and/or another component of any system detailed herein in an alternative embodiment, unless otherwise noted or unless the art does not enable such. Thus, any functionality of the prosthesis 100 can be present in the device 240 and/or another component of any system in an alternative embodiment. Thus, any disclosure of a functionality of the prosthesis 100 corresponds to structure of the device 240 and/or the another component of any system detailed herein that is configured to execute that functionality or otherwise have a functionality or otherwise to execute that method action.

Any action disclosed herein that is executed by the device 240 can be executed by the prosthesis 100 and/or another component of any system disclosed herein in an alternative embodiment, unless otherwise noted or unless the art does not enable such. Thus, any functionality of the device 240 can be present in the prosthesis 100 and/or another component of any system disclosed herein in an alternative embodiment. Thus, any disclosure of a functionality of the device 240 corresponds to structure of the prosthesis 100 and/or another component of any system disclosed herein that is configured to execute that functionality or otherwise have a functionality or otherwise to execute that method action.

Any action disclosed herein that is executed by a component of any system disclosed herein can be executed by the device 240 and/or the prosthesis 100 in an alternative embodiment, unless otherwise noted or unless the art does not enable such. Thus, any functionality of a component of the systems detailed herein can be present in the device 240 and/or the prosthesis 100 as alternative embodiment. Thus, any disclosure of a functionality of a component herein corresponds to structure of the device 240 and/or the prosthesis 100 that is configured to execute that functionality or otherwise have a functionality or otherwise to execute that method action.

It is further noted that any disclosure of a device and/or system detailed herein also corresponds to a disclosure of otherwise providing that device and/or system.

It is also noted that any disclosure herein of any process of manufacturing other providing a device corresponds to a device and/or system that results there from. Is also noted that any disclosure herein of any device and/or system corresponds to a disclosure of a method of producing or otherwise providing or otherwise making such.

Any embodiment or any feature disclosed herein can be combined with any one or more or other embodiments and/or other features disclosed herein, unless explicitly indicated and/or unless the art does not enable such. Any embodiment or any feature disclosed herein can be explicitly excluded from use with any one or more other embodiments and/or other features disclosed herein, unless explicitly indicated that such is combined and/or unless the art does not enable such exclusion.

Any disclosure herein of a method action corresponds to a disclosure of a computer readable medium having program there on code to execute one or more of those actions and also a product to execute one or more of those actions.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A sensory system, comprising:
a sensory supplement medical device input subsystem configured to receive input based on an environmental phenomenon captured by the sensory system; and
a processor configured to process data based on input into the input subsystem, wherein
the sensory system further includes a product of and/or resulting from a neural network, and
the sensory system, via the product, is configured to:
dynamically change a mapping between frequencies in the input and electrode channels of the sensory system to be stimulated, including at least shifting and/or scaling at least one frequency bin in a frequency to channel mapping of the sensory system; and
evoke a sensory percept based on the input into the input subsystem to distinguish between different environmental phenomena for a recipient of the sensory system.

2. The sensory system of claim 1, wherein:
the sensory system is a hearing system;
the environmental phenomenon captured by the sensory system is sound; and
the sensory percept is a hearing percept.

3. The sensory system of claim 2, wherein:
the sensory system is a cochlear implant system;
the environmental phenomenon captured by the sensory system is sound; and
the sensory percept is a hearing percept.

4. The sensory system of claim 1, wherein:
the sensory system is a cochlear implant system; and
the product results in stimulation of a recipient of the sensory system on a first electrode channel during a first temporal period for a given frequency and on a second electrode channel for that same frequency during a second temporal period.

5. The sensory system of claim 1, wherein:

the product adjusts a frequency domain of the data based on the input on a variable basis before reaching a map section of the sensory system.

6. The sensory system of claim 1, wherein:

the sensory system is a cochlear implant system; and the product adjusts, in real time, at least one of an amplitude, pulse width, rate of stimulation, interphase gap or maxima location of output of the cochlear implant system.

7. The sensory system of claim 1, wherein:

the product is configured to receive first data based on the input received by the input subsystem and automatically process the received first data to develop second data and output the developed second data, wherein the second data is electrode channel energies.

8. The sensory system of claim 1, wherein:

the sensory system is a hearing system, and the sensory system is configured so that the product extracts useful sound in a noisy environment beyond that which would be the case in the absence of the product, all other things being equal.

9. The sensory system of claim 1, wherein:

the sensory system is a cochlear implant system that is configured so as to obtain at least an equivalent number of input side processing filter banks that is substantially more than the number of stimulation electrode channels of the cochlear implant system.

10. The sensory system of claim 1, wherein:

the processor is a sound processor;

the sensory system is a cochlear implant system; and the sensory system is configured so that data based on the input is processed by the sound processor so that the sound processor adjusts at least one of a resulting perceived timbre or resulting perceived texture beyond that which results from frequency division and electrode channel mapping.

11. The sensory system of claim 1, wherein:

the sensory system is configured so that the product receives first data based on the input into the input subsystem and automatically process the received first data to develop second data and output the developed second data, the second data being cochlear implant channel amplitude data; and the sensory system includes an output subsystem that receives data that is based on the outputted developed second data and evokes the sensory percept based on the received data that is based on the outputted developed second data, the sensory percept being a hearing percept.

12. The sensory system of claim 1, wherein:

the product automatically determines electrode channel energies to be stimulated based on the input into the input subsystem;

the sensory system is configured to provide the determined electrode channel energies downstream of a signal processing flow of the sensory system; and the sensory system includes an output subsystem that evokes the sensory percept, which is a hearing percept, based on the determined electrode channel energies.

13. The sensory system of claim 1, wherein:

the product is part of an input side processing arrangement of an audio processing subsystem of the sensory system.

14. The sensory system of claim 1, wherein:

the product is configured to expand a dynamic range of input on a variable manner beyond that which would be the case in the absence of the product.

15. The sensory system of claim 1, wherein:

the processor is a sound processor;

the sensory system includes one or more filter banks configured to divide data based on the input into N number of frequency bins, wherein the data based on the input is audio content;

the sound processor is configured to analyze the content of the N number of frequency bins; and the sensory system is configured to, based on the analysis of the content of the N number of frequency bin, apply the content of the N number of frequency bins to M number of electrode channels, wherein M is less than N and at least one of the electrode channels is paired with two or more of the frequency bins of the N number of frequency bins which is different than that which was the case previously based solely due to an analysis using the product.

16. The sensory system of claim 1, wherein:

the sensory system is a cochlear implant system;

the cochlear implant is configured to provide frequency amplitudes of data based on the input; and the product is configured to determine electrode channel energies for the cochlear implant having electrodes that are to be stimulated based on the provided frequency amplitudes to evoke the sensory percept.

17. The sensory system of claim 1, wherein:

the sensory system is a cochlear implant system; and the product is configured to process content based on input received, by the input subsystem, during a first temporal period and process content based on input received, by the input subsystem, during a second temporal period so that respective different electrode channels of the cochlear implant are activated to stimulate a cochlea of a human to evoke respective hearing percepts, which are the sensory percepts, based on the respective contents, the different electrode channels being beyond that which results simply because the frequencies of the contents are different.

18. The sensory system of claim 1, wherein:

the product is part of an output side processing arrangement of an audio processing system of the sensory system.

19. The sensory system of claim 1, wherein:

the sensory system includes an audio processing neural network that is used by the hearing prosthesis to evoke a hearing percept based in input into the input subsystem.

\* \* \* \* \*